(12) United States Patent
Andersson et al.

(10) Patent No.: US 7,462,693 B2
(45) Date of Patent: Dec. 9, 2008

(54) VARIANTS OF THE GAMMA CHAIN OF AMPX, DNA SEQUENCES ENCODING THE SAME, AND USES THEREOF

(75) Inventors: Leif Andersson, Uppsala (SE); Christian Looft, Bokelholm (DE); Ernst Kalm, Achterwehr (DE); Denis Milan, Labege (FR); Annie Robic, Saint-Orens-de-Gameville (FR); Claire Rogel-Gaillard, Paris (FR); Nathalie Iannuccelli, Castanet-Tolosan (FR); Joel Gellin, Auzeville (FR); Pascale Le Roy, Massy (FR); Patrick Chardon, Vauhallan (FR)

(73) Assignee: Arexis AB, Göteborg (SE)

( * ) Notice: Subject to any disclaimer, the term of this patent is extended or adjusted under 35 U.S.C. 154(b) by 0 days.

(21) Appl. No.: 11/626,582

(22) Filed: Jan. 24, 2007

(65) Prior Publication Data

US 2007/0199081 A1      Aug. 23, 2007

Related U.S. Application Data

(63) Continuation of application No. 10/070,794, filed as application No. PCT/EP00/09896 on Sep. 11, 2000, now abandoned.

(30) Foreign Application Priority Data

Sep. 10, 1999  (EP) ................................. 99402236
May 18, 2000  (EP) ................................. 00401388

(51) Int. Cl.
*C07K 1/00*   (2006.01)
*C12N 15/00*  (2006.01)
*C12N 1/20*   (2006.01)
*C12P 21/06*  (2006.01)

(52) U.S. Cl. .................... 530/350; 435/69.1; 435/252.3; 435/32.1

(58) Field of Classification Search ................. 530/350; 435/69.1, 320.1, 252.3
See application file for complete search history.

(56) References Cited

U.S. PATENT DOCUMENTS

| 7,208,305 B2 | 4/2007 | Hjalm |
| 7,214,850 B2 | 5/2007 | Andersson et al. |
| 2002/0142310 A1 | 10/2002 | Anderson |
| 2003/0017470 A1 | 1/2003 | Rothschild et al. |

(Continued)

FOREIGN PATENT DOCUMENTS

WO       WO 97/25341       7/1997

(Continued)

OTHER PUBLICATIONS

Bergeron et al., "Effect of AMPK activation on muscle glucose metabolism in conscious rats," *Am. J. Physiol.*, 1999, 276:E938-E944.

(Continued)

*Primary Examiner*—Maryam Monshipouri
(74) *Attorney, Agent, or Firm*—Fish & Richardson P.C.

(57) ABSTRACT

Variants of the gamma chain of vertebrate AMP-activated kinase (AMPK), as well as nucleic acid sequences encoding the variants and use thereof for the diagnosis or treatment of dysfunction of energy metabolisms.

5 Claims, 8 Drawing Sheets

U.S. PATENT DOCUMENTS

2005/0155091 A1  7/2005  Svensson

FOREIGN PATENT DOCUMENTS

WO    WO 98/58052    12/1998

OTHER PUBLICATIONS

Carninci et al., "Normalization and Subtraction of Cap-Trapper-Selected cDNAs to Prepare Full-Length CDNA Libraries for Rapid Discovery of New Genes," *Genome Res.*, 2000, 10:1617-1630.

Cheung et al., "Characterization of AMP-activated protein kinase γ-subunit isoforms and their role in AMP binding," *Biochem. J.*, 2000, 346:659-669.

Enfält et al., "Estimated Frequency of the RN Allele in Swedish Hampshire Pigs and Comparison of Glycolytic Potential, Carcass Composition, and Technological Meat Quality Among Swedish Hampshire, Landrace, and Yorkshire Pigs," *J. Anim. Sci.*, 1997, 75:2924-2935.

Estrade et al., "Glycogen Hyperaccumulation in White Muscle Fibres of RN Carrier PIgs. A Biochemical and Ultrastructural Study," *Comp. Biochem Physiol.*, 1993, 104B(2):321-326.

Hardie et al., "The Amp-Activated/SNF1 Protein KInase Subfamily: Metabolic Sensors of the Eukaryotic Cell?" *Annu. Rev. Biochem.*, 1998, 67:821-855.

Hayashi et al., "Evidence for 5' AMP-Activated Protein Kinase Mediation of the Effect of MUscle Contraction on Glucose Transport," *Diabetes*, 1998, 47:1369-1373.

Kemp et al., "Dealing with energy demand: The AMP-activated protein kinase," *TIBS*, 1999, 24:22-25.

Le Roy et al., "Evidence for a new major gene influencing meat quality in pigs," *Genet. Res. Camb.*, 1990, 55:33-40.

Looft et al., "Mapping the porcine *RN* gene to chromosome 15," *Genet. Sel. Evol.*, 1996, 28:437-442.

Mariani et al., "A major locus (*RN*) affecting muscle glycogen content is located on pig Chromosome 15," *Mamm. Genome*, 1996, 7:52-54.

Milan et al., "Accurate mapping of the "acid meat" *RN* gene on genetic and physical maps of pig Chromasome 15, " *Mamm. Genome*, 1996, 7:47-51.

Milan et al., "A Mutation in *PRKAG3* Associated with Excess Glycogen Content in Pig Skeletal Muscle," *Science*, 2000, 288:1248-1251.

Monin and Sellier, "Pork of Low Technological Quality with a Normal Rate of Muscle pH Fall in the Immediate Post-Mortem Period: The Case of the Hampshire Breed," *Meat Science*, 1985, 13:49-63.

Monin et al., "Effects of the RN Gene on Some Traits of Muscle and Liver in Pigs," *38th International Congress of Meat Science and Technology*, Aug. 23-28, 1992, Clermont-Ferrand, France, Proceedings, vol. 3, pp. 391-394.

Robic et al., "A radiation hybrid map of teh *RN* region in pigs demonstrates conserved gene order compared with the human and mouse genomes," *Mamm. Genome*, 1999, 10:565-568.

Sun et al., "Human chromosome 3 and pig chromosome 13 show complete synteny conservation but extensive gene-order differences," *Cytogenet. Cell Genet.*, 1999, 85:273-278.

Terwilliger, "A Powerful Likelihood Method for the Analysis of Linkage Disequilibrium between Trait Loci and One or More Polymorphic Marker Loci," *Am. J. HUm. Genet.*, 1995, 56:777-787.

Treadway et al., "Enhanced Peripheral Glucose Utilization in Transgenic Mice Expressing the Human GLUT4 Gene," *J. Biol. Chem.*, 1994, 269(47):29956-29961.

GenBank Accession No. M30470 (Apr. 1993).
GenBank Accession No. U42412 (May 1996).
GenBank Accession No. W15439 (May 1996).
GenBank Accession No. W94830 (Jul. 1996).
GenBank Accession No. AA018675 (Feb. 1996).
GenBank Accession No. AA178898 (Sep. 1997).
GenBank Accession No. AC009974 (Feb. 2004).
GenBank Accession No. AF036535 (May 2001).
GenBank Accession No. AF094764 (Feb. 2004).
GenBank Accession No. AF214519 (Jun. 2000).
GenBank Accession No. AF214520 (Jun. 2000).
GenBank Accession No. AJ249976 (Apr. 2000).

```
       5'UTR       10        20        30        40        50        60        70        80
Pig TTCCTAGAGCAAGGAGAGAGCCGTTCATGGCCATCCCGAGCTGTAACCACCAGCTCAGAAAGAAGCCATGGGGACCAGGG
Hum --------------A-A-C--A-C-----------A-C------G----G---------------T--G----A-A-G-A-
              90       100       110       120       130       140       150       160
Pig GAACAAGGCCTCTAGATGGACAAGGCAGGAGGATGTAGAGGAAGGGGGGCCTCCGGGCCCGAGGGAAGGTCCCCAGTCCA
Hum -GC---A----TG--------------A--TCG--G---------A---A--A--T-A-G-----------G-----
             170       180       190       200       210       220       230       240
Pig GGCCAGTTGCTGAGTCCACCGGGCAGGAGGCCACATTCCCCAAGGCCACACCCTTGGCCCAAGCCGCTCCCTTGGCCGAG
Hum -----AC----------------T--------------------A--------------T-----T-A---...T----G-
             250       260       270       280       290       300       310       320
Pig GTGGACAACCCCCCAACAGAGCGGGACATCCTCCCCTCTGACTGTGCAGCCTCAGCCTCCGACTCCAACACAGACCATCT
Hum ----G--CT--A--------G-T-----TG----------------A----------TG-A-G------G-----TG--G-
             330       340       350       360       370       380       390       400
Pig GGATCTGGGCATAGAGTTCTCAGCCTCGGCGGCGTCGGGGGATGAGCTTG...GGCTGGTGGAAGAGAAGCCAGCCCCGT
Hum ---G----C--CG------C-----A-A-A---C-G--A-TG------A-AAG-C---C---------G---T----T--
             410       420       430       440       450       460       470 5'UTR
Pig GCCCATCCCCAGAGGTGCTGTTACCCAGGCTGGGCTGGGATGATGAGCTGCAGAAGCCGGGGGCCCAGGTCTAC
Hum ---TG-----GC---CC-CA--T----A---------------C--A----G---A--C--C------A-----
     CDS                                        10                                      20
Pig ATG CAC TTC ATG CAG GAG CAC ACC TGC TAC GAT GCC ATG GCG ACC AGC TCC AAA CTG GTC
    Met His Phe Met Gln Glu His Thr Cys Tyr Asp Ala Met Ala Thr Ser Ser Lys Leu Val
Hum --- -G- --- --- --- --- --- --- --- --- --- --- --- --A --T --- --- --G --A ---
      - Arg -   -   -   -   -   -   -   -   -   -   -   -   -   -   -   -   -   -
                                  30                                        40
Pig ATC TTC GAC ACC ATG CTG GAG ATC AAG AAG GCC TTC TTT GCC CTG GTG GCC AAC GGC GTC
    Ile Phe Asp Thr Met Leu Glu Ile Lys Lys Ala Phe Phe Ala Leu Val Ala Asn Gly Val
Hum --- --- --- --- --- --- --- --- --- --- --- --- --- --T --- --- --- --- --T --G
      -   -   -   -   -   -   -   -   -   -   -   -   -   -   -   -   -   -   -   -
                                  50                                        60
Pig CGA GCG GCA CCT TTG TGG GAC AGC AAG AAG CAG AGC TTC GTG GGG ATG CTG ACC ATC ACA
    Arg Ala Ala Pro Leu Trp Asp Ser Lys Lys Gln Ser Phe Val Gly Met Leu Thr Ile Thr
Hum --G --A --C --- C-A --- --- --- --- --- --- --T --- --- --- --- --- --- --- --T
      -   -   -   -   -   -   -   -   -   -   -   -   -   -   -   -   -   -   -   -
                                  70                                        80
Pig GAC TTC ATC TTG GTG CTG CAC CGC TAT TAC AGG TCC CCC CTG GTC CAG ATC TAC GAG ATT
    Asp Phe Ile Leu Val Leu His Arg Tyr Tyr Arg Ser Pro Leu Val Gln Ile Tyr Glu Ile
Hum --- --- --- C-- --- --- --T --- --C --- --- --- --- --- --- --- --T --- --- ---
      -   -   -   -   -   -   -   -   -   -   -   -   -   -   -   -   -   -   -   -
                                  90                                       100
Pig GAA GAA CAT AAG ATT GAG ACC TGG AGG GAG ATC TAC CTT CAA GGC TGC TTC AAG CCT CTG
    Glu Glu His Lys Ile Glu Thr Trp Arg Glu Ile Tyr Leu Gln Gly Cys Phe Lys Pro Leu
Hum --- C-- --- --- --- --- --- --- --- --- --- --- --G --- --- --- --- --- --- ---
      - Gln -   -   -   -   -   -   -   -   -   -   -   -   -   -   -   -   -   -
                                 110                                       120
Pig GTC TCC ATC TCT CCC AAT GAC AGC CTG TTC GAA GCT GTC TAC GCC CTC ATC AAG AAC CGG
    Val Ser Ile Ser Pro Asn Asp Ser Leu Phe Glu Ala Val Tyr Ala Leu Ile Lys Asn Arg
Hum --- --- --- --- --T --- --T --- --- --T --- --- --- A-- --- --- --- --- --- ---
      -   -   -   -   -   -   -   -   -   -   -   -   -   - Thr -   -   -   -   -
                                 130                                       140
Pig ATC CAC CGC CTG CCG GTC CTG GAC CCT GTC TCC GGG GCT GTG CTC CAC ATC CTC ACA CAT
    Ile His Arg Leu Pro Val Leu Asp Pro Val Ser Gly Ala Val Leu His Ile Leu Thr His
Hum --- --T --- --- --T --T --T --- --G --A --C AAC --A --- --- --- --- --- --- --C
      -   -   -   -   -   -   -   -   -   -   - Asn -   -   -   -   -   -   -   -
                                 150                                       160
Pig AAG CGG CTT CTC AAG TTC CTG CAC ATC TTT GGC ACC CTG CTG CCC CGG CCC TCC TTC CTC
    Lys Arg Leu Leu Lys Phe Leu His Ile Phe Gly Thr Leu Leu Pro Arg Pro Ser Phe Leu
Hum --A --C --G --- --- --- --- --- --- --T T-- --- --- --- --- --- --- --- --- ---
      -   -   -   -   -   -   -   -   - Ser -   -   -   -   -   -   -   -   -   -
```

Figure 2

```
                               170                                                        180
Pig TAC CGC ACC ATC CAA GAT TTG GGC ATC GGC ACA TTC CGA GAC TTG GCC GTG GTG CTG GAA
    Tyr Arg Thr Ile Gln Asp Leu Gly Ile Gly Thr Phe Arg Asp Leu Ala Val Val Leu Glu
Hum --- --- --T --- --- --- --- --- --- --- --- --- --- --- --T --- --- --- --G
     -   -   -   -   -   -   -   -   -   -   -   -   -   -   -   -   -   -   -   -
                               190                                                        200
Pig ACG GCG CCC ATC CTG ACC GCA CTG GAC ATC TTC GTG GAC CGG CGT GTG TCT GCG CTG CCT
    Thr Ala Pro Ile Leu Thr Ala Leu Asp Ile Phe Val Asp Arg Arg Val Ser Ala Leu Pro
Hum --A --A --- --- --- --T --- --- --- --- --T --- --- --- --- --- --- --A --- ---
     -   -   -   -   -   -   -   -   -   -   -   -   -   -   -   -   -   -   -   -
                               210                                                        220
Pig GTG GTC AAC GAA ACT GGA CAG GTA GTG GGC CTC TAC TCT CGC TTT GAT GTG ATC CAC CTG
    Val Val Asn Glu Thr Gly Gln Val Val Gly Leu Tyr Ser Arg Phe Asp Val Ile His Leu
Hum --- --- --- --- TG- --T --- --C --- --- --- --T --C --- --- --- --T --- --- ---
     -   -   -   -  Cys  -   -   -   -   -   -   -   -   -   -   -   -   -   -   -
                               230                                                        240
Pig GCT GCC CAA CAA ACA TAC AAC CAC CTG GAC ATG AAT GTG GGA GAA GCC CTG AGG CAG CGG
    Ala Ala Gln Gln Thr Tyr Asn His Leu Asp Met Asn Val Gly Glu Ala Leu Arg Gln Arg
Hum --- --- --G --- --C --- --- --- --- --- --- -G- --- --- --- --- --- --- --- A--
     -   -   -   -   -   -   -   -   -   -   -  Ser  -   -   -   -   -   -   -   -
                               250                                                        260
Pig ACA CTG TGT CTG GAA GGC GTC CTT TCC TGC CAG CCC CAC GAG ACC TTG GGG GAA GTC ATT
    Thr Leu Cys Leu Glu Gly Val Leu Ser Cys Gln Pro His Glu Thr Leu Gly Glu Val Ile
Hum --- --A --- --- --G --A --- --- --- --- --- --- --- --- -G- --- --- --- --G --C
     -   -   -   -   -   -   -   -   -   -   -   -   -   -  Ser  -   -   -   -   -
                               270                                                        280
Pig GAC CGG ATT GTC CGG GAA CAG GTG CAC CGC CTG GTG CTC GTG GAT GAG ACC CAG CAC CTT
    Asp Arg Ile Val Arg Glu Gln Val His Arg Leu Val Leu Val Asp Glu Thr Gln His Leu
Hum --- A-- --- -CT --- --G --- --A --- A-G --- --- --A --- --C --- --- --- --T --C
     -   -   -  Ala  -   -   -   -   -   -   -   -   -   -   -   -   -   -   -   -
                               290                                                        300
Pig CTG GGC GTG GTG TCC CTC TCT GAC ATC CTT CAG GCT CTG GTG CTC AGC CCT GCT GGA ATT
    Leu Gly Val Val Ser Leu Ser Asp Ile Leu Gln Ala Leu Val Leu Ser Pro Ala Gly Ile
Hum T-- --- --- --C --- --- --C --- --- --- --- --A --- --- --- --- --- --- --C --C
     -   -   -   -   -   -   -   -   -   -   -   -   -   -   -   -   -   -   -   -
                                CDS
Pig GAT GCC CTC GGG GCC TGA
    Asp Ala Leu Gly Ala ***
Hum --- --- --- --- --- ---
     -   -   -   -   -
   3'UTR   10         20         30         40         50         60         70         80
Pig GAACCTTGGAACCTTTGCTCTCAGGCCACCTGGCACACCTGGAAGCCAGTGAAGGGAGCCGTGGACTCAGCTCTCACTTC
Hum ---GA-CT--GT-C-CAA---C--A----A---.------.---------A-------A-T...--AGAA-----.---T---
              90        100        110        120        130        140        150        160
Pig CCCTCAGCCCCACTTGCTGGTCTGGCTCTTGTTCAGGTAGGCTCCGCCCGGGGC.....CCCTGGCCTCAGCATCAGCCC
Hum ---A.-C---A-T--------TCA---A-GA------CTTCT--A---TTCCAAAATTG--T-T----T-.-T-GT--T-
             170        180        190        200        210        220        230        240
Pig CTCAGTCTCCCT.GGGCACCCAGATCTCAGACTGGGGCACCCTGAAGATG.GGAGTGGCCCAGCTTATAGCTGAGCAG.C
Hum -.---AAC--T-C-----TG-CC-GTG--CCA----..-TGA----AT-AA----AACAG-T-AG-CA----TG-AG-T-
             250        260        270        280        290        300        310        320
Pig CTTGTG..AAATCTACCAGCATCAAGACT...CACTGTGGGACCACTGCTTTG...TCCCATTCTCAGCTGAAATGAT.G
Hum -C---AACC-G-GGC--T--G--T-CCC-AGGG-CA-C--T-CT-CA---CCGCCCA----C--GC-GC-----CTG-G-C-
             330        340        350        360        370        380        390        400
Pig GAGGGCCTCATAAGAGGGGTGGACAGGG..CTGGAGTAGAGGCCAGATCAGTGACGT..GCCTTCAGG....ACCTCCG
Hum --T-----C--GTG-...-TT-A-T------TT-----T-CCTC-GTTTC-GG-CT--C-AT-G------CCTTC-G----T
```

Figure 2 (cont.)

```
            410       420       430       440       450       460       470       480
Pig GGGAGTTAGAGCTGCCCTCTCTCAGTT.......CAGTTCCCCCCTGCTGAGAATG.TCCCTGGAAGGAAGCCAGTTAAT
Hum ------CCC-----TTG-.--C---CAACGTCGC--C-G---T---A--CTCC-G-C-TTG-CATTTC---G-T-C-G-.
            490       500       510       520       530       540       550       560
Pig AAACCTTGGTTGGATGGAATTTCCACACTCG..................................................
Hum --TG--GCA--TC-G--G...-----CA-G-AGCAGCCGTTATTTATAGAACTGCCTGTTGGAGGTGGGGAGTCCTCCCT
            570       580       590       600       610       620       630       640
Pig .................................................................................
Hum CCATTCTTGTCCAGAAAACTCCTTAGCTCTCGCAGTGAGCCATGTTCTTAGTCTCCAGGGATGGATGGCCTTGTATATGG
            650       660       670       680       690       700       710       720
Pig .................................................................................
Hum ACCCCTGAGAATGAGCAATTGAGAAAACAAAACAAAAGGAACAATCCATGAACTTAGATTTTATTGGTTTCACTCAAAAT
            730       740
Pig ..................
Hum GCTGCAGTCATTTGACCTG
```

Figure 2 (cont.)

```
PigG3   MSFLEQGESRSWPSRAVTTSSERSHGDQGNKASRWTRQEDVEEGGPPGPREGPQSRPVAESTGQEATFPKATPLAQAAPLAEVDNPPTERDILPSDCAAS   100
HumG3   ------EN-S---P---S----IR-KRRA-L-----KS---E---QG---R----T-----L------T----D-.G-GT---GW-C----T--        200

PigG3   ASDSNTDHLDLGIEFSASAASGDEL.GLVEEKPAPCPSPEVLLPRLGWDDELQKPGAQVYMHFMQEHTCYDAMATSSKLVIFDTMLEIKKAFFALVANGV
HumG3   -AG-S--DVE-AT--P-TE-WEC--E--L--R--L-L--QAPF-K-----R-----I--R-------------------V---S--QV---------
HumG1                            METVIS-DSSPAVENEHPQ-TPESNNS--TS--KS-R---LIP-------V---T--QV---------T--
HumG2                            AALGPAEAGM-EKLEFE-EAVEDSESG---R--RS-K---IVP-------V---T-QV------------
Dros                             RDSRGLPVADPFLEKVNLSD-EEDDS-IFVK-FRF-K---LIP-A---V---Q-LV-----Y----Y--
Snf4                                   MK-TQDSQEKVSIEQQLAVES..IRK-LNSK-S--VLPV-YR-IVL-S--LV---SLNV-LQ-SI     300
                                                                               CBS1→

PigG3   RAAPLWDSKKQSFVGMLTTTDFILVLHRYYRSPLVQIYEIEBHKIETWREIYLQGCFKPL..VSTSPNDSLFEAVYALIKNRIHRLPVLDPVSGA....V
HumG3   -------------------------------------------------Q-------------------T--------------------N----
HumG1   ------------------------NI------K-A-----L--------------V---DS--------C----A--D-SS--R-K----I--E-N---T
HumG2   -----E--T--SL---NI------K-M-----L--------------L--ET------N---DA--D---S----K-----I---I--N---A
Dros    ------E--Q---------------KI-QM--K--NASMEQL---LD--DV.-HNQVM------G-DA--YD-IKI--HS---------I--AT-N--
Snf4    VS------TSR-A-L-T----N-IQY-FSN-D.KFELVDKLQLDGLKD-ERALGVDQ-DTA--H-SRP------CLKMLES-SG-I-LI-QDEETHREI
                                                         CBS2→

PigG3   LHILTHKRLLKFLHIFGTLLPRPSFLYRTIQDLIGTFRDLAVVLETAPILTALDIFVDRRVSALPVVNETGQVVGLYSRFDVIHLAAQQTYNHLDMNVG  400
HumG3   ------------------------------------------------------------------------------------------C-----
HumG1   -Y------I-----KL-I-EF-K-E-MSKSLEE-Q----YANI-M-RT-T-VYV--G---QH---------D-K-R--DI--K---N--EK--N--VS-T
HumG2   -Y------I-----QL-MSDM-K-A-MKQNLDE------YHNI-FIHPDT--IK--N--E-I-------D-S-K--DI--K---N--EK--N--IT-T
Dros    -Y------I-R--FLYINE--K-AYMQKSLRE--K---YNNIETAD--TS-I--KK--E-----L-DSD-RL-DI-AK---N--EK--D--VSLR
Snf4    VSV---QY-I---VALNCRE..TH---KIP-G--N-I-QDNMKSCQM-T-VIDVIQMLTQG---SV-IID-N-YLINV--EAY--LG-IKGGI-D-SLS--
                CBS4→                                                                                    472

PigG3   EALRQRTLCLEGVLSCQPHETLGEVIDRIVREQVHRLVLVDETQHLLGVVSLSDIIQALVLSPAGIDALGA*
HumG3   ----------------------------S------A-----------------------------------
HumG1   K--QH-SHYF----K-YL----ETI-N-L-EAE-----V---NDVVK--I------------TGGEKKP*
HumG2   Q--QH-SQYF----VK-NKL-I-ETIV----AE-----V--ADSIV-II------------I-T---AKQETETE*
Dros    K-NEH-NEWF---QK-NLD-S-YTIME----AE-----V--NRKVI-II--------LY---R-S-EGV
Snf4    ---MR-SDDF---YT-TKNDK-STIM-N-RKAR---FFV--DVGR-V--LT-----KYIL-GSN*
```

Figure 3

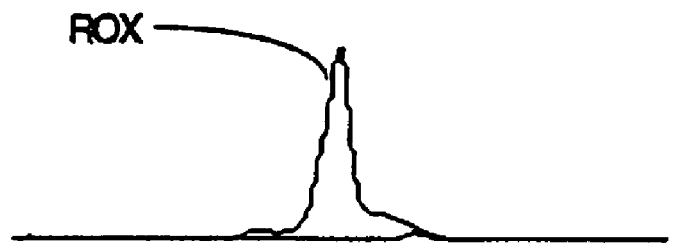
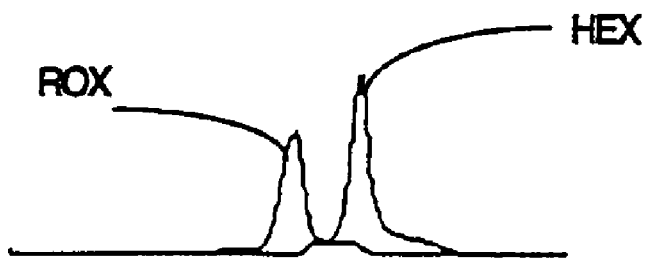
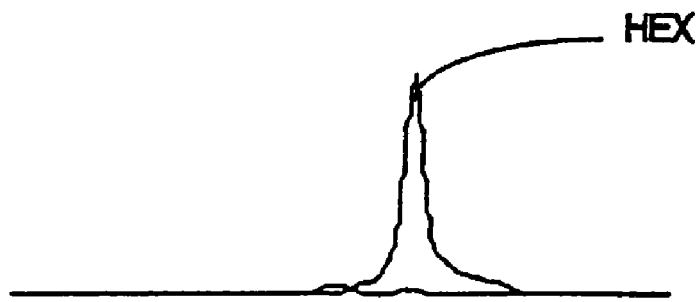
Figure 6

SEQUENCE LISTING

```
<160> NUMBER OF SEQ ID NOS: 42

<210> SEQ ID NO 1
<211> LENGTH: 1867
<212> TYPE: DNA
<213> ORGANISM: Sus scrofa
<220> FEATURE:
<221> NAME/KEY: CDS
<222> LOCATION: (472)..(1389)

<400> SEQUENCE: 1
ttcctagagc aaggagagag ccgttcatgg ccatcccgag ctgtaaccac cagctcagaa      60
agaagccatg gggaccaggg gaacaaggcc tctagatgga caaggcagga ggatgtagag     120
gaaggggggc ctccgggccc gagggaaggt ccccagtcca ggccagttgc tgagtccacc     180
gggcaggagg ccacattccc caaggccaca cccttggccc aagccgctcc cttggccgag     240
gtggacaacc ccccaacaga gcgggacatc ctcccctctg actgtgcagc ctcagcctcc     300
gactccaaca cagaccatct ggatctgggc atagagttct cagcctcggc ggcgtcgggg     360
gatgagcttg ggctggtgga agagaagcca gccccgtgcc catccccaga ggtgctgtta     420
cccaggctgg gctgggatga tgagctgcag aagccggggg cccaggtcta c atg cac      477
                                                         Met His
                                                           1 ttc atg cag gag cac acc tgc tac gat gcc atg gcg acc agc tcc aaa      525
Phe Met Gln Glu His Thr Cys Tyr Asp Ala Met Ala Thr Ser Ser Lys
      5                  10                  15 ctg gtc atc ttc gac acc atg ctg gag atc aag aag gcc ttc ttt gcc      573
Leu Val Ile Phe Asp Thr Met Leu Glu Ile Lys Lys Ala Phe Phe Ala
 20                  25                  30 ctg gtg gcc aac ggc gtc cga gcg gca cct ttg tgg gac agc aag aag      621
Leu Val Ala Asn Gly Val Arg Ala Ala Pro Leu Trp Asp Ser Lys Lys
 35                  40                  45                  50 cag agc ttc gtg ggg atg ctg acc atc aca gac ttc atc ttg gtg ctg      669
Gln Ser Phe Val Gly Met Leu Thr Ile Thr Asp Phe Ile Leu Val Leu
              55                  60                  65 cac cgc tat tac agg tcc ccc ctg gtc cag atc tac gag att gaa gaa      717
His Arg Tyr Tyr Arg Ser Pro Leu Val Gln Ile Tyr Glu Ile Glu Glu
          70                  75                  80 cat aag att gag acc tgg agg gag atc tac ctt caa ggc tgc ttc aag      765
His Lys Ile Glu Thr Trp Arg Glu Ile Tyr Leu Gln Gly Cys Phe Lys
      85                  90                  95 cct ctg gtc tcc atc tct ccc aat gac agc ctg ttc gaa gct gtc tac      813
Pro Leu Val Ser Ile Ser Pro Asn Asp Ser Leu Phe Glu Ala Val Tyr
100                 105                 110 gcc ctc atc aag aac cgg atc cac cgc ctg ccg gtc ctg gac cct gtc      861
```

```
Ala Leu Ile Lys Asn Arg Ile His Arg Leu Pro Val Leu Asp Pro Val
115                 120                 125                 130 tcc ggg gct gtg ctc cac atc ctc aca cat aag cgg ctt ctc aag ttc      909
Ser Gly Ala Val Leu His Ile Leu Thr His Lys Arg Leu Leu Lys Phe
                135                 140                 145 ctg cac atc ttt ggc acc ctg ctg ccc cgg ccc tcc ttc ctc tac cgc      957
Leu His Ile Phe Gly Thr Leu Leu Pro Arg Pro Ser Phe Leu Tyr Arg
                150                 155                 160 acc atc caa gat ttg ggc atc ggc aca ttc cga gac ttg gcc gtg gtg     1005
Thr Ile Gln Asp Leu Gly Ile Gly Thr Phe Arg Asp Leu Ala Val Val
                165                 170                 175 ctg gaa acg gcg ccc atc ctg acc gca ctg gac atc ttc gtg gac cgg     1053
Leu Glu Thr Ala Pro Ile Leu Thr Ala Leu Asp Ile Phe Val Asp Arg
                180                 185                 190 cgt gtg tct gcg ctg cct gtg gtc aac gaa act gga cag gta gtg ggc     1101
Arg Val Ser Ala Leu Pro Val Val Asn Glu Thr Gly Gln Val Val Gly
195                 200                 205                 210 ctc tac tct cgc ttt gat gtg atc cac ctg gct gcc caa caa aca tac     1149
Leu Tyr Ser Arg Phe Asp Val Ile His Leu Ala Ala Gln Gln Thr Tyr
                215                 220                 225 aac cac ctg gac atg aat gtg gga gaa gcc ctg agg cag cgg aca ctg     1197
Asn His Leu Asp Met Asn Val Gly Glu Ala Leu Arg Gln Arg Thr Leu
                230                 235                 240 tgt ctg gaa ggc gtc ctt tcc tgc cag ccc cac gag acc ttg ggg gaa     1245
Cys Leu Glu Gly Val Leu Ser Cys Gln Pro His Glu Thr Leu Gly Glu
                245                 250                 255 gtc att gac cgg att gtc cgg gaa cag gtg cac cgc ctg gtg ctc gtg     1293
Val Ile Asp Arg Ile Val Arg Glu Gln Val His Arg Leu Val Leu Val
260                 265                 270 gat gag acc cag cac ctt ctg ggc gtg gtg tcc ctc tct gac atc ctt     1341
Asp Glu Thr Gln His Leu Leu Gly Val Val Ser Leu Ser Asp Ile Leu
275                 280                 285                 290 cag gct ctg gtg ctc agc cct gct gga att gat gcc ctc ggg gcc tga     1389
Gln Ala Leu Val Leu Ser Pro Ala Gly Ile Asp Ala Leu Gly Ala
                295                 300                 305 gaaccttgga acctttgctc tcaggccacc tggcacacct ggaagccagt gaagggagcc   1449
gtggactcag ctctcacttc ccctcagccc cacttgctgg tctggctctt gttcaggtag   1509
gctccgcccg ggcccctggg cctcagcatc agccctcag tctccctggg cacccagatc    1569
tcagactggg gcaccctgaa gatgggagtg cccagctta tagctgagca gccttgtgaa    1629
atctaccagc atcaagactc actgtgggac cactgctttg tcccattctc agctgaaatg   1689
atggagggcc tcataagagg ggtggacagg gcctggagta gaggccagat cagtgacgtg   1749
ccttcaggac ctccggggag ttagagctgc cctctctcag ttcagttccc ccctgctgag   1809
aatgtccctg gaaggaagcc agttaataaa ccttggttgg atggaatttc cacactcg    1867
```

<210> SEQ ID NO 2
<211> LENGTH: 305
<212> TYPE: PRT
<213> ORGANISM: Sus scrofa

<400> SEQUENCE: 2

```
Met His Phe Met Gln Glu His Thr Cys Tyr Asp Ala Met Ala Thr Ser
1               5                   10                  15

Ser Lys Leu Val Ile Phe Asp Thr Met Leu Glu Ile Lys Lys Ala Phe
                20                  25                  30

Phe Ala Leu Val Ala Asn Gly Val Arg Ala Ala Pro Leu Trp Asp Ser
            35                  40                  45
```

```
Lys Lys Gln Ser Phe Val Gly Met Leu Thr Ile Thr Asp Phe Ile Leu
     50                  55                  60
Val Leu His Arg Tyr Tyr Arg Ser Pro Leu Val Gln Ile Tyr Glu Ile
 65                  70                  75                  80
Glu Glu His Lys Ile Glu Thr Trp Arg Glu Ile Tyr Leu Gln Gly Cys
                 85                  90                  95
Phe Lys Pro Leu Val Ser Ile Ser Pro Asn Asp Ser Leu Phe Glu Ala
            100                 105                 110
Val Tyr Ala Leu Ile Lys Asn Arg Ile His Arg Leu Pro Val Leu Asp
        115                 120                 125
Pro Val Ser Gly Ala Val Leu His Ile Leu Thr His Lys Arg Leu Leu
    130                 135                 140
Lys Phe Leu His Ile Phe Gly Thr Leu Leu Pro Arg Pro Ser Phe Leu
145                 150                 155                 160
Tyr Arg Thr Ile Gln Asp Leu Gly Ile Gly Thr Phe Arg Asp Leu Ala
                165                 170                 175
Val Val Leu Glu Thr Ala Pro Ile Leu Thr Ala Leu Asp Ile Phe Val
            180                 185                 190
Asp Arg Arg Val Ser Ala Leu Pro Val Val Asn Glu Thr Gly Gln Val
        195                 200                 205
Val Gly Leu Tyr Ser Arg Phe Asp Val Ile His Leu Ala Ala Gln Gln
    210                 215                 220
Thr Tyr Asn His Leu Asp Met Asn Val Gly Glu Ala Leu Arg Gln Arg
225                 230                 235                 240
Thr Leu Cys Leu Glu Gly Val Leu Ser Cys Gln Pro His Glu Thr Leu
                245                 250                 255
Gly Glu Val Ile Asp Arg Ile Val Arg Glu Gln Val His Arg Leu Val
            260                 265                 270
Leu Val Asp Glu Thr Gln His Leu Leu Gly Val Val Ser Leu Ser Asp
        275                 280                 285
Ile Leu Gln Ala Leu Val Leu Ser Pro Ala Gly Ile Asp Ala Leu Gly
    290                 295                 300
Ala
305

<210> SEQ ID NO 3
<211> LENGTH: 2109
<212> TYPE: DNA
<213> ORGANISM: Homo sapiens
<220> FEATURE:
<221> NAME/KEY: CDS
<222> LOCATION: (472)..(1389)

<400> SEQUENCE: 3
ttcctagagc aagaaaacag cagctcatgg ccatcaccag ctgtgaccag cagctcagaa      60
agaatccgtg ggaaacggag ggccaaagcc ttgagatgga caaggcagaa gtcggtggag     120 gaagggagc caccaggtca ggggaaggt ccccggtcca ggccaactgc tgagtccacc      180
gggctggagg ccacattccc caagaccaca cccttggctc aagctgatcc tgccggggtg     240
ggcactccac caacagggtg ggactgcctc ccctctgact gtacagcctc agctgcaggc     300
tccagcacag atgatgtgga gctggccacg gagttcccag ccacagaggc ctgggagtgt     360
gagctagaag gctgctgga agagaggcct gccctgtgcc tgtccccgca ggccccattt     420
cccaagctgg gctgggatga cgaactgcgg aaacccggcg cccagatcta c atg cgc     477
                                                        Met Arg
```

-continued

```
                                                                        1
ttc atg cag gag cac acc tgc tac gat gcc atg gca act agc tcc aag        525
Phe Met Gln Glu His Thr Cys Tyr Asp Ala Met Ala Thr Ser Ser Lys
      5                  10                  15 cta gtc atc ttc gac acc atg ctg gag atc aag aag gcc ttc ttt gct        573
Leu Val Ile Phe Asp Thr Met Leu Glu Ile Lys Lys Ala Phe Phe Ala
 20                  25                  30 ctg gtg gcc aac ggt gtg cgg gca gcc cct cta tgg gac agc aag aag        621
Leu Val Ala Asn Gly Val Arg Ala Ala Pro Leu Trp Asp Ser Lys Lys
 35                  40                  45                  50 cag agc ttt gtg ggg atg ctg acc atc act gac ttc atc ctg gtg ctg        669
Gln Ser Phe Val Gly Met Leu Thr Ile Thr Asp Phe Ile Leu Val Leu
             55                  60                  65 cat cgc tac tac agg tcc ccc ctg gtc cag atc tat gag att gaa caa        717
His Arg Tyr Tyr Arg Ser Pro Leu Val Gln Ile Tyr Glu Ile Glu Gln
         70                  75                  80 cat aag att gag acc tgg agg gag atc tac ctg caa ggc tgc ttc aag        765
His Lys Ile Glu Thr Trp Arg Glu Ile Tyr Leu Gln Gly Cys Phe Lys
     85                  90                  95 cct ctg gtc tcc atc tct cct aat gat agc ctg ttt gaa gct gtc tac        813
Pro Leu Val Ser Ile Ser Pro Asn Asp Ser Leu Phe Glu Ala Val Tyr
100                 105                 110 acc ctc atc aag aac cgg atc cat cgc ctg cct gtt ctt gac ccg gtg        861
Thr Leu Ile Lys Asn Arg Ile His Arg Leu Pro Val Leu Asp Pro Val
115                 120                 125                 130 tca ggc aac gta ctc cac atc ctc aca cac aaa cgc ctg ctc aag ttc        909
Ser Gly Asn Val Leu His Ile Leu Thr His Lys Arg Leu Leu Lys Phe
                135                 140                 145 ctg cac atc ttt ggt tcc ctg ctg ccc cgg ccc tcc ttc ctc tac cgc        957
Leu His Ile Phe Gly Ser Leu Leu Pro Arg Pro Ser Phe Leu Tyr Arg
            150                 155                 160 act atc caa gat ttg ggc atc ggc aca ttc cga gac ttg gct gtg gtg       1005
Thr Ile Gln Asp Leu Gly Ile Gly Thr Phe Arg Asp Leu Ala Val Val
        165                 170                 175 ctg gag aca gca ccc atc ctg act gca ctg gac atc ttt gtg gac cgg       1053
Leu Glu Thr Ala Pro Ile Leu Thr Ala Leu Asp Ile Phe Val Asp Arg
180                 185                 190 cgt gtg tct gca ctg cct gtg gtc aac gaa tgt ggt cag gtc gtg ggc       1101
Arg Val Ser Ala Leu Pro Val Val Asn Glu Cys Gly Gln Val Val Gly
195                 200                 205                 210 ctc tat tcc cgc ttt gat gtg att cac ctg gct gcc cag caa acc tac       1149
Leu Tyr Ser Arg Phe Asp Val Ile His Leu Ala Ala Gln Gln Thr Tyr
                215                 220                 225 aac cac ctg gac atg agt gtg gga gaa gcc ctg agg cag agg aca cta       1197
Asn His Leu Asp Met Ser Val Gly Glu Ala Leu Arg Gln Arg Thr Leu
            230                 235                 240 tgt ctg gag gga gtc ctt tcc tgc cag ccc cac gag agc ttg ggg gaa       1245
Cys Leu Glu Gly Val Leu Ser Cys Gln Pro His Glu Ser Leu Gly Glu
        245                 250                 255 gtg atc gac agg att gct cgg gag cag gta cac agg ctg gtg cta gtg       1293
Val Ile Asp Arg Ile Ala Arg Glu Gln Val His Arg Leu Val Leu Val
260                 265                 270 gac gag acc cag cat ctc ttg ggc gtg gtc tcc ctc tcc gac atc ctt       1341
Asp Glu Thr Gln His Leu Leu Gly Val Val Ser Leu Ser Asp Ile Leu
275                 280                 285                 290 cag gca ctg gtg ctc agc cct gct ggc atc gat gcc ctc ggg gcc tga       1389
Gln Ala Leu Val Leu Ser Pro Ala Gly Ile Asp Ala Leu Gly Ala
                295                 300                 305 gaagatctga gtcctcaatc ccaagccaac tgcacactgg aagccaatga aggaattgag     1449
```

```
aacagcttca tttccccaac cccaatttgc tggttcagct atgattcagg cttcttcagc    1509
cttccaaaat tgcctttgcc ttacttgtgc tcccagaacc cttcgggcat gcccagtgca    1569
ccatgggatg atgaaattaa ggagaacagc tgagtcaagc ttggaggtcc ctgaaccaga    1629
ggcactagga ttaccccagg gccatctgtg ctccatgccc gccatcccc ttgccgcctg     1689 actgggtcgg atggcccag tgggtttagt cagggcttct ggattcctcg gtttctgggc     1749
tacctatggc ttcagccttc agctcctggg agtcccagct gttgttccca gcaacgtcgc    1809
cactgccctc ctactctcca ggctttgtca tttcaaggct gctgaaatgc tgcatttcag    1869
gggccaccat ggagcagccg ttatttatag aactgcctgt tggaggtggg gagtcctccc    1929
tccattcttg tccagaaaac tccttagctc tcgcagtgag ccatgttctt agtctccagg    1989
gatggatggc cttgtatatg gaccCCtgag aatgagcaat tgagaaaaca aaacaaaagg    2049
aacaatccat gaacttagat tttattggtt tcactcaaaa tgctgcagtc atttgacctg    2109
```

<210> SEQ ID NO 4
<211> LENGTH: 305
<212> TYPE: PRT
<213> ORGANISM: Homo sapiens

<400> SEQUENCE: 4

```
Met Arg Phe Met Gln Glu His Thr Cys Tyr Asp Ala Met Ala Thr Ser
  1               5                  10                  15

Ser Lys Leu Val Ile Phe Asp Thr Met Leu Glu Ile Lys Lys Ala Phe
             20                  25                  30

Phe Ala Leu Val Ala Asn Gly Val Arg Ala Ala Pro Leu Trp Asp Ser
         35                  40                  45

Lys Lys Gln Ser Phe Val Gly Met Leu Thr Ile Thr Asp Phe Ile Leu
     50                  55                  60

Val Leu His Arg Tyr Tyr Arg Ser Pro Leu Val Gln Ile Tyr Glu Ile
 65                  70                  75                  80

Glu Gln His Lys Ile Glu Thr Trp Arg Glu Ile Tyr Leu Gln Gly Cys
                 85                  90                  95

Phe Lys Pro Leu Val Ser Ile Ser Pro Asn Asp Ser Leu Phe Glu Ala
            100                 105                 110

Val Tyr Thr Leu Ile Lys Asn Arg Ile His Arg Leu Pro Val Leu Asp
        115                 120                 125

Pro Val Ser Gly Asn Val Leu His Ile Leu Thr His Lys Arg Leu Leu
    130                 135                 140

Lys Phe Leu His Ile Phe Gly Ser Leu Leu Pro Arg Pro Ser Phe Leu
145                 150                 155                 160

Tyr Arg Thr Ile Gln Asp Leu Gly Ile Gly Thr Phe Arg Asp Leu Ala
                165                 170                 175

Val Val Leu Glu Thr Ala Pro Ile Leu Thr Ala Leu Asp Ile Phe Val
            180                 185                 190

Asp Arg Arg Val Ser Ala Leu Pro Val Val Asn Glu Cys Gly Gln Val
        195                 200                 205

Val Gly Leu Tyr Ser Arg Phe Asp Val Ile His Leu Ala Ala Gln Gln
    210                 215                 220

Thr Tyr Asn His Leu Asp Met Ser Val Gly Glu Ala Leu Arg Gln Arg
225                 230                 235                 240

Thr Leu Cys Leu Glu Gly Val Leu Ser Cys Gln Pro His Glu Ser Leu
                245                 250                 255
```

```
Gly Glu Val Ile Asp Arg Ile Ala Arg Glu Gln Val His Arg Leu Val
            260                 265                 270

Leu Val Asp Glu Thr Gln His Leu Leu Gly Val Val Ser Leu Ser Asp
        275                 280                 285

Ile Leu Gln Ala Leu Val Leu Ser Pro Ala Gly Ile Asp Ala Leu Gly
    290                 295                 300

Ala
305

<210> SEQ ID NO 5
<211> LENGTH: 20
<212> TYPE: DNA
<213> ORGANISM: Sus scrofa

<400> SEQUENCE: 5
ggaatttcaa gtcagccaac                                              20

<210> SEQ ID NO 6
<211> LENGTH: 20
<212> TYPE: DNA
<213> ORGANISM: Sus scrofa

<400> SEQUENCE: 6
cttcaaaaga ccgtgctact                                              20

<210> SEQ ID NO 7
<211> LENGTH: 20
<212> TYPE: DNA
<213> ORGANISM: Sus scrofa

<400> SEQUENCE: 7
ctgggaacct ctatatgctg                                              20

<210> SEQ ID NO 8
<211> LENGTH: 20
<212> TYPE: DNA
<213> ORGANISM: Sus scrofa

<400> SEQUENCE: 8
tagggaaata caaatcacag                                              20

<210> SEQ ID NO 9
<211> LENGTH: 20
<212> TYPE: DNA
<213> ORGANISM: Sus scrofa

<400> SEQUENCE: 9
ctccagctca caggatgaca                                              20

<210> SEQ ID NO 10
<211> LENGTH: 26
<212> TYPE: DNA
<213> ORGANISM: Sus scrofa

<400> SEQUENCE: 10
gtttctgcag ctttagcatc tattcc                                       26

<210> SEQ ID NO 11
<211> LENGTH: 20
<212> TYPE: DNA
<213> ORGANISM: Sus scrofa

<400> SEQUENCE: 11
```

```
gaagtatcct gggcttctga                                              20

<210> SEQ ID NO 12
<211> LENGTH: 26
<212> TYPE: DNA
<213> ORGANISM: Sus scrofa

<400> SEQUENCE: 12
gtttctccag gtttccagac atccac                                       26

<210> SEQ ID NO 13
<211> LENGTH: 20
<212> TYPE: DNA
<213> ORGANISM: Sus scrofa

<400> SEQUENCE: 13
gcttctgtct gcccctactt                                              20

<210> SEQ ID NO 14
<211> LENGTH: 26
<212> TYPE: DNA
<213> ORGANISM: Sus scrofa

<400> SEQUENCE: 14
gtttctaagt tctactgtaa gacacc                                       26

<210> SEQ ID NO 15
<211> LENGTH: 20
<212> TYPE: DNA
<213> ORGANISM: Sus scrofa

<400> SEQUENCE: 15
ccaagctgtg gtggctgaat                                              20

<210> SEQ ID NO 16
<211> LENGTH: 20
<212> TYPE: DNA
<213> ORGANISM: Sus scrofa

<400> SEQUENCE: 16
cagcacagca gtgccaccta                                              20

<210> SEQ ID NO 17
<211> LENGTH: 19
<212> TYPE: DNA
<213> ORGANISM: Sus scrofa

<400> SEQUENCE: 17
caaactcttc taggcgtgt                                               19

<210> SEQ ID NO 18
<211> LENGTH: 26
<212> TYPE: DNA
<213> ORGANISM: Sus scrofa

<400> SEQUENCE: 18
gtttctggaa cttccatatg ccatgg                                       26

<210> SEQ ID NO 19
<211> LENGTH: 20
<212> TYPE: DNA
<213> ORGANISM: Sus scrofa
```

```
<400> SEQUENCE: 19
agggtggatg gtaggcttca                                              20

<210> SEQ ID NO 20
<211> LENGTH: 20
<212> TYPE: DNA
<213> ORGANISM: Sus scrofa

<400> SEQUENCE: 20
gtctcgctcc tgaaggaagt                                              20

<210> SEQ ID NO 21
<211> LENGTH: 20
<212> TYPE: DNA
<213> ORGANISM: Sus scrofa

<400> SEQUENCE: 21
agtcacgtgg ccatgctatc                                              20

<210> SEQ ID NO 22
<211> LENGTH: 20
<212> TYPE: DNA
<213> ORGANISM: Sus scrofa

<400> SEQUENCE: 22
ctcaactgga ttgagtcagt                                              20

<210> SEQ ID NO 23
<211> LENGTH: 20
<212> TYPE: DNA
<213> ORGANISM: Sus scrofa

<400> SEQUENCE: 23
ttggcgcaac tgttatttct                                              20

<210> SEQ ID NO 24
<211> LENGTH: 19
<212> TYPE: DNA
<213> ORGANISM: Sus scrofa

<400> SEQUENCE: 24
aggcaaagga agagcacag                                               19

<210> SEQ ID NO 25
<211> LENGTH: 18
<212> TYPE: DNA
<213> ORGANISM: Sus scrofa

<400> SEQUENCE: 25
agccgtgggc atcgttgg                                                18

<210> SEQ ID NO 26
<211> LENGTH: 21
<212> TYPE: DNA
<213> ORGANISM: Sus scrofa

<400> SEQUENCE: 26
agaaggagac agacagggcga                                             21

<210> SEQ ID NO 27
<211> LENGTH: 1873
<212> TYPE: DNA
<213> ORGANISM: Sus scrofa
```

<220> FEATURE:
<221> NAME/KEY: CDS
<222> LOCATION: (1)..(1395)

<400> SEQUENCE: 27

```
atg agc ttc cta gag caa gga gag agc cgt tca tgg cca tcc cga gct      48
Met Ser Phe Leu Glu Gln Gly Glu Ser Arg Ser Trp Pro Ser Arg Ala
 1               5                  10                  15 gta acc acc agc tca gaa aga agc cat ggg gac cag ggg aac aag gcc      96
Val Thr Thr Ser Ser Glu Arg Ser His Gly Asp Gln Gly Asn Lys Ala
             20                  25                  30 tct aga tgg aca agg cag gag gat gta gag gaa ggg ggg cct ccg ggc     144
Ser Arg Trp Thr Arg Gln Glu Asp Val Glu Glu Gly Gly Pro Pro Gly
         35                  40                  45 ccg agg gaa ggt ccc cag tcc agg cca gtt gct gag tcc acc ggg cag     192
Pro Arg Glu Gly Pro Gln Ser Arg Pro Val Ala Glu Ser Thr Gly Gln
     50                  55                  60 gag gcc aca ttc ccc aag gcc aca ccc ttg gcc caa gcc gct ccc ttg     240
Glu Ala Thr Phe Pro Lys Ala Thr Pro Leu Ala Gln Ala Ala Pro Leu
 65                  70                  75                  80 gcc gag gtg gac aac ccc cca aca gag cgg gac atc ctc ccc tct gac     288
Ala Glu Val Asp Asn Pro Pro Thr Glu Arg Asp Ile Leu Pro Ser Asp
                 85                  90                  95 tgt gca gcc tca gcc tcc gac tcc aac aca gac cat ctg gat ctg ggc     336
Cys Ala Ala Ser Ala Ser Asp Ser Asn Thr Asp His Leu Asp Leu Gly
            100                 105                 110 ata gag ttc tca gcc tcg gcg gcg tcg ggg gat gag ctt ggg ctg gtg     384
Ile Glu Phe Ser Ala Ser Ala Ala Ser Gly Asp Glu Leu Gly Leu Val
        115                 120                 125 gaa gag aag cca gcc ccg tgc cca tcc cca gag gtg ctg tta ccc agg     432
Glu Glu Lys Pro Ala Pro Cys Pro Ser Pro Glu Val Leu Leu Pro Arg
    130                 135                 140 ctg ggc tgg gat gat gag ctg cag aag ccg ggg gcc cag gtc tac atg     480
Leu Gly Trp Asp Asp Glu Leu Gln Lys Pro Gly Ala Gln Val Tyr Met
145                 150                 155                 160 cac ttc atg cag gag cac acc tgc tac gat gcc atg gcg acc agc tcc     528
His Phe Met Gln Glu His Thr Cys Tyr Asp Ala Met Ala Thr Ser Ser
                165                 170                 175 aaa ctg gtc atc ttc gac acc atg ctg gag atc aag aag gcc ttc ttt     576
Lys Leu Val Ile Phe Asp Thr Met Leu Glu Ile Lys Lys Ala Phe Phe
            180                 185                 190 gcc ctg gtg gcc aac ggc gtc cga gcg gca cct ttg tgg gac agc aag     624
Ala Leu Val Ala Asn Gly Val Arg Ala Ala Pro Leu Trp Asp Ser Lys
        195                 200                 205 aag cag agc ttc gtg ggg atg ctg acc atc aca gac ttc atc ttg gtg     672
Lys Gln Ser Phe Val Gly Met Leu Thr Ile Thr Asp Phe Ile Leu Val
    210                 215                 220 ctg cac cgc tat tac agg tcc ccc ctg gtc cag atc tac gag att gaa     720
Leu His Arg Tyr Tyr Arg Ser Pro Leu Val Gln Ile Tyr Glu Ile Glu
225                 230                 235                 240 gaa cat aag att gag acc tgg agg gag atc tac ctt caa ggc tgc ttc     768
Glu His Lys Ile Glu Thr Trp Arg Glu Ile Tyr Leu Gln Gly Cys Phe
                245                 250                 255 aag cct ctg gtc tcc atc tct ccc aat gac agc ctg ttc gaa gct gtc     816
Lys Pro Leu Val Ser Ile Ser Pro Asn Asp Ser Leu Phe Glu Ala Val
            260                 265                 270 tac gcc ctc atc aag aac cgg atc cac cgc ctg ccg gtc ctg gac cct     864
Tyr Ala Leu Ile Lys Asn Arg Ile His Arg Leu Pro Val Leu Asp Pro
        275                 280                 285 gtc tcc ggg gct gtg ctc cac atc ctc aca cat aag cgg ctt ctc aag     912
```

```
                Val Ser Gly Ala Val Leu His Ile Leu Thr His Lys Arg Leu Leu Lys
                    290                 295                 300 ttc ctg cac atc ttt ggc acc ctg ctg ccc cgg ccc tcc ttc ctc tac        960
Phe Leu His Ile Phe Gly Thr Leu Leu Pro Arg Pro Ser Phe Leu Tyr
305                 310                 315                 320 cgc acc atc caa gat ttg ggc atc ggc aca ttc cga gac ttg gcc gtg       1008
Arg Thr Ile Gln Asp Leu Gly Ile Gly Thr Phe Arg Asp Leu Ala Val
                325                 330                 335 gtg ctg gaa acg gcg ccc atc ctg acc gca ctg gac atc ttc gtg gac       1056
Val Leu Glu Thr Ala Pro Ile Leu Thr Ala Leu Asp Ile Phe Val Asp
            340                 345                 350 cgg cgt gtg tct gcg ctg cct gtg gtc aac gaa act gga cag gta gtg       1104
Arg Arg Val Ser Ala Leu Pro Val Val Asn Glu Thr Gly Gln Val Val
        355                 360                 365 ggc ctc tac tct cgc ttt gat gtg atc cac ctg gct gcc caa caa aca       1152
Gly Leu Tyr Ser Arg Phe Asp Val Ile His Leu Ala Ala Gln Gln Thr
    370                 375                 380 tac aac cac ctg gac atg aat gtg gga gaa gcc ctg agg cag cgg aca       1200
Tyr Asn His Leu Asp Met Asn Val Gly Glu Ala Leu Arg Gln Arg Thr
385                 390                 395                 400 ctg tgt ctg gaa ggc gtc ctt tcc tgc cag ccc cac gag acc ttg ggg       1248
Leu Cys Leu Glu Gly Val Leu Ser Cys Gln Pro His Glu Thr Leu Gly
                405                 410                 415 gaa gtc att gac cgg att gtc cgg gaa cag gtg cac cgc ctg gtg ctc       1296
Glu Val Ile Asp Arg Ile Val Arg Glu Gln Val His Arg Leu Val Leu
            420                 425                 430 gtg gat gag acc cag cac ctt ctg ggc gtg gtg tcc ctc tct gac atc       1344
Val Asp Glu Thr Gln His Leu Leu Gly Val Val Ser Leu Ser Asp Ile
        435                 440                 445 ctt cag gct ctg gtg ctc agc cct gct gga att gat gcc ctc ggg gcc       1392
Leu Gln Ala Leu Val Leu Ser Pro Ala Gly Ile Asp Ala Leu Gly Ala
    450                 455                 460 tga gaaccttgga acctttgctc tcaggccacc tggcacacct ggaagccagt            1445
gaagggagcc gtggactcag ctctcacttc ccctcagccc cacttgctgg tctggctctt     1505
gttcaggtag gctccgcccg gggccctggg cctcagcatc agcccctcag tctccctggg     1565
cacccagatc tcagactggg gcaccctgaa gatgggagtg cccagctta tagctgagca     1625 gccttgtgaa atctaccagc atcaagacta ctgtgggac cactgctttg tcccattctc     1685
agctgaaatg atggagggcc tcataagagg ggtggacagg gcctggagta gaggccagat    1745
cagtgacgtg ccttcaggac ctccggggag ttagagctgc cctctctcag ttcagttccc    1805
ccctgctgag aatgtccctg gaaggaagcc agttaataaa ccttggttgg atggaatttg    1865
gagagtcg                                                              1873

<210> SEQ ID NO 28
<211> LENGTH: 464
<212> TYPE: PRT
<213> ORGANISM: Sus scrofa

<400> SEQUENCE: 28

Met Ser Phe Leu Glu Gln Gly Glu Ser Arg Ser Trp Pro Ser Arg Ala
1               5                   10                  15

Val Thr Thr Ser Ser Glu Arg Ser His Gly Asp Gln Gly Asn Lys Ala
            20                  25                  30

Ser Arg Trp Thr Arg Gln Glu Asp Val Glu Glu Gly Gly Pro Pro Gly
        35                  40                  45

Pro Arg Glu Gly Pro Gln Ser Arg Pro Val Ala Glu Ser Thr Gly Gln
```

```
              50                  55                  60
Glu Ala Thr Phe Pro Lys Ala Thr Pro Leu Ala Gln Ala Ala Pro Leu
 65                  70                  75                  80

Ala Glu Val Asp Asn Pro Pro Thr Glu Arg Asp Ile Leu Pro Ser Asp
                 85                  90                  95

Cys Ala Ala Ser Ala Ser Asp Ser Asn Thr Asp His Leu Asp Leu Gly
                100                 105                 110

Ile Glu Phe Ser Ala Ser Ala Ala Ser Gly Asp Glu Leu Gly Leu Val
                115                 120                 125

Glu Glu Lys Pro Ala Pro Cys Pro Ser Pro Glu Val Leu Leu Pro Arg
130                 135                 140

Leu Gly Trp Asp Asp Glu Leu Gln Lys Pro Gly Ala Gln Val Tyr Met
145                 150                 155                 160

His Phe Met Gln Glu His Thr Cys Tyr Asp Ala Met Ala Thr Ser Ser
                165                 170                 175

Lys Leu Val Ile Phe Asp Thr Met Leu Glu Ile Lys Lys Ala Phe Phe
                180                 185                 190

Ala Leu Val Ala Asn Gly Val Arg Ala Ala Pro Leu Trp Asp Ser Lys
                195                 200                 205

Lys Gln Ser Phe Val Gly Met Leu Thr Ile Thr Asp Phe Ile Leu Val
210                 215                 220

Leu His Arg Tyr Tyr Arg Ser Pro Leu Val Gln Ile Tyr Glu Ile Glu
225                 230                 235                 240

Glu His Lys Ile Glu Thr Trp Arg Glu Ile Tyr Leu Gln Gly Cys Phe
                245                 250                 255

Lys Pro Leu Val Ser Ile Ser Pro Asn Asp Ser Leu Phe Glu Ala Val
                260                 265                 270

Tyr Ala Leu Ile Lys Asn Arg Ile His Arg Leu Pro Val Leu Asp Pro
                275                 280                 285

Val Ser Gly Ala Val Leu His Ile Leu Thr His Lys Arg Leu Leu Lys
                290                 295                 300

Phe Leu His Ile Phe Gly Thr Leu Leu Pro Arg Pro Ser Phe Leu Tyr
305                 310                 315                 320

Arg Thr Ile Gln Asp Leu Gly Ile Gly Thr Phe Arg Asp Leu Ala Val
                325                 330                 335

Val Leu Glu Thr Ala Pro Ile Leu Thr Ala Leu Asp Ile Phe Val Asp
                340                 345                 350

Arg Arg Val Ser Ala Leu Pro Val Val Asn Glu Thr Gly Gln Val Val
                355                 360                 365

Gly Leu Tyr Ser Arg Phe Asp Val Ile His Leu Ala Ala Gln Gln Thr
370                 375                 380

Tyr Asn His Leu Asp Met Asn Val Gly Glu Ala Leu Arg Gln Arg Thr
385                 390                 395                 400

Leu Cys Leu Glu Gly Val Leu Ser Cys Gln Pro His Glu Thr Leu Gly
                405                 410                 415

Glu Val Ile Asp Arg Ile Val Arg Glu Gln Val His Arg Leu Val Leu
                420                 425                 430

Val Asp Glu Thr Gln His Leu Leu Gly Val Val Ser Leu Ser Asp Ile
                435                 440                 445

Leu Gln Ala Leu Val Leu Ser Pro Ala Gly Ile Asp Ala Leu Gly Ala
450                 455                 460
```

<210> SEQ ID NO 29

<211> LENGTH: 2115
<212> TYPE: DNA
<213> ORGANISM: Homo sapiens
<220> FEATURE:
<221> NAME/KEY: CDS
<222> LOCATION: (1)..(1395)

<400> SEQUENCE: 29

| | | | | | | | | | | | | | | | | |
|---|---|---|---|---|---|---|---|---|---|---|---|---|---|---|---|---|
| atg | agc | ttc | cta | gag | caa | gaa | aac | agc | agc | tca | tgg | cca | tca | cca | gct | 48 |
| Met | Ser | Phe | Leu | Glu | Gln | Glu | Asn | Ser | Ser | Ser | Trp | Pro | Ser | Pro | Ala | |
| 1 | | | | 5 | | | | | 10 | | | | | 15 | | |
| gtg | acc | agc | agc | tca | gaa | aga | atc | cgt | ggg | aaa | cgg | agg | gcc | aaa | gcc | 96 |
| Val | Thr | Ser | Ser | Ser | Glu | Arg | Ile | Arg | Gly | Lys | Arg | Arg | Ala | Lys | Ala | |
| | | | 20 | | | | | 25 | | | | | 30 | | | |
| ttg | aga | tgg | aca | agg | cag | aag | tcg | gtg | gag | gaa | ggg | gag | cca | cca | ggt | 144 |
| Leu | Arg | Trp | Thr | Arg | Gln | Lys | Ser | Val | Glu | Glu | Gly | Glu | Pro | Pro | Gly | |
| | | 35 | | | | | 40 | | | | | 45 | | | | |
| cag | ggg | gaa | ggt | ccc | cgg | tcc | agg | cca | act | gct | gag | tcc | acc | ggg | ctg | 192 |
| Gln | Gly | Glu | Gly | Pro | Arg | Ser | Arg | Pro | Thr | Ala | Glu | Ser | Thr | Gly | Leu | |
| | 50 | | | | | 55 | | | | | 60 | | | | | |
| gag | gcc | aca | ttc | ccc | aag | acc | aca | ccc | ttg | gct | caa | gct | gat | cct | gcc | 240 |
| Glu | Ala | Thr | Phe | Pro | Lys | Thr | Thr | Pro | Leu | Ala | Gln | Ala | Asp | Pro | Ala | |
| 65 | | | | | 70 | | | | | 75 | | | | | 80 | |
| ggg | gtg | ggc | act | cca | cca | aca | ggg | tgg | gac | tgc | ctc | ccc | tct | gac | tgt | 288 |
| Gly | Val | Gly | Thr | Pro | Pro | Thr | Gly | Trp | Asp | Cys | Leu | Pro | Ser | Asp | Cys | |
| | | | | 85 | | | | | 90 | | | | | 95 | | |
| aca | gcc | tca | gct | gca | ggc | tcc | agc | aca | gat | gat | gtg | gag | ctg | gcc | acg | 336 |
| Thr | Ala | Ser | Ala | Ala | Gly | Ser | Ser | Thr | Asp | Asp | Val | Glu | Leu | Ala | Thr | |
| | | | 100 | | | | | 105 | | | | | 110 | | | |
| gag | ttc | cca | gcc | aca | gag | gcc | tgg | gag | tgt | gag | cta | gaa | ggc | ctg | ctg | 384 |
| Glu | Phe | Pro | Ala | Thr | Glu | Ala | Trp | Glu | Cys | Glu | Leu | Glu | Gly | Leu | Leu | |
| | | 115 | | | | | 120 | | | | | 125 | | | | |
| gaa | gag | agg | cct | gcc | ctg | tgc | ctg | tcc | ccg | cag | gcc | cca | ttt | ccc | aag | 432 |
| Glu | Glu | Arg | Pro | Ala | Leu | Cys | Leu | Ser | Pro | Gln | Ala | Pro | Phe | Pro | Lys | |
| | 130 | | | | | 135 | | | | | 140 | | | | | |
| ctg | ggc | tgg | gat | gac | gaa | ctg | cgg | aaa | ccc | ggc | gcc | cag | atc | tac | atg | 480 |
| Leu | Gly | Trp | Asp | Asp | Glu | Leu | Arg | Lys | Pro | Gly | Ala | Gln | Ile | Tyr | Met | |
| 145 | | | | | 150 | | | | | 155 | | | | | 160 | |
| cgc | ttc | atg | cag | gag | cac | acc | tgc | tac | gat | gcc | atg | gca | act | agc | tcc | 528 |
| Arg | Phe | Met | Gln | Glu | His | Thr | Cys | Tyr | Asp | Ala | Met | Ala | Thr | Ser | Ser | |
| | | | | 165 | | | | | 170 | | | | | 175 | | |
| aag | cta | gtc | atc | ttc | gac | acc | atg | ctg | gag | atc | aag | aag | gcc | ttc | ttt | 576 |
| Lys | Leu | Val | Ile | Phe | Asp | Thr | Met | Leu | Glu | Ile | Lys | Lys | Ala | Phe | Phe | |
| | | | 180 | | | | | 185 | | | | | 190 | | | |
| gct | ctg | gtg | gcc | aac | ggt | gtg | cgg | gca | gcc | cct | cta | tgg | gac | agc | aag | 624 |
| Ala | Leu | Val | Ala | Asn | Gly | Val | Arg | Ala | Ala | Pro | Leu | Trp | Asp | Ser | Lys | |
| | | 195 | | | | | 200 | | | | | 205 | | | | |
| aag | cag | agc | ttt | gtg | ggg | atg | ctg | acc | atc | act | gac | ttc | atc | ctg | gtg | 672 |
| Lys | Gln | Ser | Phe | Val | Gly | Met | Leu | Thr | Ile | Thr | Asp | Phe | Ile | Leu | Val | |
| | 210 | | | | | 215 | | | | | 220 | | | | | |
| ctg | cat | cgc | tac | tac | agg | tcc | ccc | ctg | gtc | cag | atc | tat | gag | att | gaa | 720 |
| Leu | His | Arg | Tyr | Tyr | Arg | Ser | Pro | Leu | Val | Gln | Ile | Tyr | Glu | Ile | Glu | |
| 225 | | | | | 230 | | | | | 235 | | | | | 240 | |
| caa | cat | aag | att | gag | acc | tgg | agg | gag | atc | tac | ctg | caa | ggc | tgc | ttc | 768 |
| Gln | His | Lys | Ile | Glu | Thr | Trp | Arg | Glu | Ile | Tyr | Leu | Gln | Gly | Cys | Phe | |
| | | | | 245 | | | | | 250 | | | | | 255 | | |
| aag | cct | ctg | gtc | tcc | atc | tct | cct | aat | gat | agc | ctg | ttt | gaa | gct | gtc | 816 |
| Lys | Pro | Leu | Val | Ser | Ile | Ser | Pro | Asn | Asp | Ser | Leu | Phe | Glu | Ala | Val | |
| | | | 260 | | | | | 265 | | | | | 270 | | | |
| tac | acc | ctc | atc | aag | aac | cgg | atc | cat | cgc | ctg | cct | gtt | ctt | gac | ccg | 864 |
| Tyr | Thr | Leu | Ile | Lys | Asn | Arg | Ile | His | Arg | Leu | Pro | Val | Leu | Asp | Pro | |

```
                275               280                285
gtg tca ggc aac gta ctc cac atc ctc aca cac aaa cgc ctg ctc aag         912
Val Ser Gly Asn Val Leu His Ile Leu Thr His Lys Arg Leu Leu Lys
    290                 295                 300 ttc ctg cac atc ttt ggt tcc ctg ctg ccc cgg ccc tcc ttc ctc tac         960
Phe Leu His Ile Phe Gly Ser Leu Leu Pro Arg Pro Ser Phe Leu Tyr
305                 310                 315                 320 cgc act atc caa gat ttg ggc atc ggc aca ttc cga gac ttg gct gtg        1008
Arg Thr Ile Gln Asp Leu Gly Ile Gly Thr Phe Arg Asp Leu Ala Val
                325                 330                 335 gtg ctg gag aca gca ccc atc ctg act gca ctg gac atc ttt gtg gac        1056
Val Leu Glu Thr Ala Pro Ile Leu Thr Ala Leu Asp Ile Phe Val Asp
            340                 345                 350 cgg cgt gtg tct gca ctg cct gtg gtc aac gaa tgt ggt cag gtc gtg        1104
Arg Arg Val Ser Ala Leu Pro Val Val Asn Glu Cys Gly Gln Val Val
        355                 360                 365 ggc ctc tat tcc cgc ttt gat gtg att cac ctg gct gcc cag caa acc        1152
Gly Leu Tyr Ser Arg Phe Asp Val Ile His Leu Ala Ala Gln Gln Thr
    370                 375                 380 tac aac cac ctg gac atg agt gtg gga gaa gcc ctg agg cag agg aca        1200
Tyr Asn His Leu Asp Met Ser Val Gly Glu Ala Leu Arg Gln Arg Thr
385                 390                 395                 400 cta tgt ctg gag gga gtc ctt tcc tgc cag ccc cac gag agc ttg ggg        1248
Leu Cys Leu Glu Gly Val Leu Ser Cys Gln Pro His Glu Ser Leu Gly
                405                 410                 415 gaa gtg atc gac agg att gct cgg gag cag gta cac agg ctg gtg cta        1296
Glu Val Ile Asp Arg Ile Ala Arg Glu Gln Val His Arg Leu Val Leu
            420                 425                 430 gtg gac gag acc cag cat ctc ttg ggc gtg gtc tcc ctc tcc gac atc        1344
Val Asp Glu Thr Gln His Leu Leu Gly Val Val Ser Leu Ser Asp Ile
        435                 440                 445 ctt cag gca ctg gtg ctc agc cct gct ggc atc gat gcc ctc ggg gcc        1392
Leu Gln Ala Leu Val Leu Ser Pro Ala Gly Ile Asp Ala Leu Gly Ala
    450                 455                 460 tga gaagatctga gtcctcaatc ccaagccaac tgcacactgg aagccaatga             1445
aggaattgag aacagcttca tttccccaac cccaatttgc tggttcagct atgattcagg      1505
cttcttcagc cttccaaaat tgcctttgcc ttacttgtgc tcccagaacc cttcgggcat      1565
gcccagtgca ccatgggatg atgaaattaa ggagaacagc tgagtcaagc ttggaggtcc      1625
ctgaaccaga ggcactagga ttaccccagg ccatctgtg ctccatgccc gcccatcccc       1685
ttgccgcctg actgggtcgg atggcccag tgggtttagt cagggcttct ggattcctcg       1745
gtttctgggc tacctatggc ttcagccttc agctcctggg agtcccagct gttgttccca      1805
gcaacgtcgc cactgccctc ctactctcca ggctttgtca tttcaaggct gctgaaatgc      1865
tgcatttcag gggccaccat ggagcagccg ttatttatag aactgcctgt tggaggtggg      1925
gagtcctccc tccattcttg tccagaaaac tccttagctc tcgcagtgag ccatgttctt      1985
agtctccagg gatggatggc cttgtatatg gaccctgag aatgagcaat tgagaaaaca       2045
aaacaaaagg aacaatccat gaacttagat tttattggtt tcactcaaaa tgctgcagtc      2105
atttgacctg                                                             2115
```

<210> SEQ ID NO 30
<211> LENGTH: 464
<212> TYPE: PRT
<213> ORGANISM: Homo sapiens

<400> SEQUENCE: 30

-continued

```
Met Ser Phe Leu Glu Gln Glu Asn Ser Ser Trp Pro Ser Pro Ala
 1               5                  10                 15

Val Thr Ser Ser Ser Glu Arg Ile Arg Gly Lys Arg Ala Lys Ala
                20                  25                 30

Leu Arg Trp Thr Arg Gln Lys Ser Val Glu Gly Glu Pro Pro Gly
            35                  40                 45

Gln Gly Glu Gly Pro Arg Ser Arg Pro Thr Ala Glu Ser Thr Gly Leu
 50                  55                  60

Glu Ala Thr Phe Pro Lys Thr Thr Pro Leu Ala Gln Ala Asp Pro Ala
 65                  70                  75                 80

Gly Val Gly Thr Pro Thr Gly Trp Asp Cys Leu Pro Ser Asp Cys
                85                  90                 95

Thr Ala Ser Ala Ala Gly Ser Ser Thr Asp Asp Val Glu Leu Ala Thr
                100                 105                110

Glu Phe Pro Ala Thr Glu Ala Trp Glu Cys Glu Leu Glu Gly Leu Leu
                115                 120                125

Glu Glu Arg Pro Ala Leu Cys Leu Ser Pro Gln Ala Pro Phe Pro Lys
 130                 135                 140

Leu Gly Trp Asp Asp Glu Leu Arg Lys Pro Gly Ala Gln Ile Tyr Met
145                 150                 155                160

Arg Phe Met Gln Glu His Thr Cys Tyr Asp Ala Met Ala Thr Ser Ser
                165                 170                 175

Lys Leu Val Ile Phe Asp Thr Met Leu Glu Ile Lys Lys Ala Phe Phe
                180                 185                 190

Ala Leu Val Ala Asn Gly Val Arg Ala Ala Pro Leu Trp Asp Ser Lys
                195                 200                 205

Lys Gln Ser Phe Val Gly Met Leu Thr Ile Thr Asp Phe Ile Leu Val
 210                 215                 220

Leu His Arg Tyr Tyr Arg Ser Pro Leu Val Gln Ile Tyr Glu Ile Glu
225                 230                 235                240

Gln His Lys Ile Glu Thr Trp Arg Glu Ile Tyr Leu Gln Gly Cys Phe
                245                 250                 255

Lys Pro Leu Val Ser Ile Ser Pro Asn Asp Ser Leu Phe Glu Ala Val
                260                 265                 270

Tyr Thr Leu Ile Lys Asn Arg Ile His Arg Leu Pro Val Leu Asp Pro
                275                 280                 285

Val Ser Gly Asn Val Leu His Ile Leu Thr His Lys Arg Leu Leu Lys
 290                 295                 300

Phe Leu His Ile Phe Gly Ser Leu Leu Pro Arg Pro Ser Phe Leu Tyr
305                 310                 315                320

Arg Thr Ile Gln Asp Leu Gly Ile Gly Thr Phe Arg Asp Leu Ala Val
                325                 330                 335

Val Leu Glu Thr Ala Pro Ile Leu Thr Ala Leu Asp Ile Phe Val Asp
                340                 345                 350

Arg Arg Val Ser Ala Leu Pro Val Val Asn Glu Cys Gly Gln Val Val
                355                 360                 365

Gly Leu Tyr Ser Arg Phe Asp Val Ile His Leu Ala Ala Gln Gln Thr
                370                 375                 380

Tyr Asn His Leu Asp Met Ser Val Gly Glu Ala Leu Arg Gln Arg Thr
385                 390                 395                400

Leu Cys Leu Glu Gly Val Leu Ser Cys Gln Pro His Glu Ser Leu Gly
                405                 410                 415
```

```
Glu Val Ile Asp Arg Ile Ala Arg Glu Gln Val His Arg Leu Val Leu
            420                 425                 430

Val Asp Glu Thr Gln His Leu Leu Gly Val Val Ser Leu Ser Asp Ile
        435                 440                 445

Leu Gln Ala Leu Val Leu Ser Pro Ala Gly Ile Asp Ala Leu Gly Ala
    450                 455                 460

<210> SEQ ID NO 31
<211> LENGTH: 2022
<212> TYPE: DNA
<213> ORGANISM: Sus scrofa

<400> SEQUENCE: 31
atggagcttg ccgagctaga gcaggcactg cgcagggtcc cggggtcccg ggggggctgg      60
gagctggagc aactgaggcc agagggcaga gggcccacca ctgcggatac tccctcctgg     120
agcagcctcg ggggacctaa gcatcaagag atgagcttcc tagagcaagg agagagccgt     180
tcatggccat cccgagctgt aaccaccagc tcagaaagaa gccatgggga ccaggggaac     240
aaggcctcta gatggacaag gcaggaggat gtagaggaag ggggcctcc gggcccgagg      300 gaaggtcccc agtccaggcc agttgctgag tccaccgggc aggaggccac attccccaag     360
gccacaccct tggcccaagc cgctcccttg gccgaggtgg acaacccccc aacagagcgg     420
gacatcctcc cctctgactg tgcagcctca gcctccgact ccaacacaga ccatctggat     480
ctgggcatag agttctcagc ctcggcggcg tcggggatg agcttgggct ggtggaagag      540
aagccagccc cgtgcccatc cccagaggtg ctgttaccca ggctgggctg gatgatgag      600 ctgcagaagc cggggcccca ggtctacatg cacttcatgc aggagcacac ctgctacgat     660
gccatggcga ccagctccaa actggtcatc ttcgacacca tgctggagat caagaaggcc     720
ttctttgccc tggtggccaa cggcgtccga gcggcacctt gtgggacag caagaagcag      780 agcttcgtgg ggatgctgac catcacagac ttcatcttgg tgctgcaccg ctattacagg     840
tcccccctgg tccagatcta cgagattgaa gaacataaga ttgagacctg gagggagatc     900
taccttcaag ctgcttcaa gcctctggtc tccatctctc caatgacag cctgttcgaa       960 gctgtctacg ccctcatcaa gaaccggatc caccgcctgc cggtcctgga ccctgtctcc    1020
ggggctgtgc tccacatcct cacacataag cggcttctca gttcctgca catctttggc     1080 accctgctgc cccggccctc cttcctctac cgcaccatcc aagatttggg catcggcaca    1140
ttccgagact ggccgtggt gctggaaacg cgcccatcc tgaccgcact ggacatcttc      1200
gtggaccggc gtgtgtctgc gctgcctgtg gtcaacgaaa ctggacaggt agtgggcctc    1260
tactctcgct tgatgtgat ccacctggct gcccaacaaa catacaacca cctggacatg     1320
aatgtgggag aagccctgag gcagcggaca ctgtgtctgg aaggcgtcct ttcctgccag    1380
ccccacgaga ccttgggga agtcattgac cggattgtcc gggaacaggt gcaccgcctg    1440
gtgctcgtgg atgagaccca gcaccttctg ggcgtggtgt ccctctctga catccttcag    1500
gctctggtgc tcagccctgc tggaattgat gccctcgggg cctgagaacc ttggaacctt    1560
tgctctcagg ccacctggca cacctggaag ccagtgaagg gagccgtgga ctcagctctc    1620 acttccctc agcccactt gctggtctgg ctcttgttca ggtaggctcc gcccggggcc      1680
cctggcctca gcatcagccc ctcagtctcc ctgggcaccc agatctcaga ctggggcacc    1740
ctgaagatgg gagtggccca gcttatagct gagcagcctt gtgaaatcta ccagcatcaa    1800
gactcactgt gggaccactg ctttgtccca ttctcagctg aaatgatgga gggcctcata    1860
```

```
agaggggtgg acagggcctg gagtagaggc cagatcagtg acgtgccttc aggacctccg    1920
gggagttaga gctgccctct ctcagttcag ttcccccctg ctgagaatgt ccctggaagg    1980
aagccagtta ataaaccttg gttggatgga atttggagag tc                      2022
```

```
<210> SEQ ID NO 32
<211> LENGTH: 514
<212> TYPE: PRT
<213> ORGANISM: Sus scrofa

<400> SEQUENCE: 32
```

```
Met Glu Leu Ala Glu Leu Glu Gln Ala Leu Arg Arg Val Pro Gly Ser
 1               5                  10                  15

Arg Gly Gly Trp Glu Leu Glu Gln Leu Arg Pro Glu Gly Arg Gly Pro
                20                  25                  30

Thr Thr Ala Asp Thr Pro Ser Trp Ser Ser Leu Gly Gly Pro Lys His
            35                  40                  45

Gln Glu Met Ser Phe Leu Glu Gln Gly Glu Ser Arg Ser Trp Pro Ser
        50                  55                  60

Arg Ala Val Thr Thr Ser Ser Glu Arg Ser His Gly Asp Gln Gly Asn
 65                  70                  75                  80

Lys Ala Ser Arg Trp Thr Arg Gln Glu Asp Val Glu Glu Gly Gly Pro
                85                  90                  95

Pro Gly Pro Arg Glu Gly Pro Gln Ser Arg Pro Val Ala Glu Ser Thr
            100                 105                 110

Gly Gln Glu Ala Thr Phe Pro Lys Ala Thr Pro Leu Ala Gln Ala Ala
        115                 120                 125

Pro Leu Ala Glu Val Asp Asn Pro Pro Thr Glu Arg Asp Ile Leu Pro
    130                 135                 140

Ser Asp Cys Ala Ala Ser Ala Ser Asp Ser Asn Thr Asp His Leu Asp
145                 150                 155                 160

Leu Gly Ile Glu Phe Ser Ala Ser Ala Ser Gly Asp Glu Leu Gly
                165                 170                 175

Leu Val Glu Glu Lys Pro Ala Pro Cys Pro Ser Pro Glu Val Leu Leu
            180                 185                 190

Pro Arg Leu Gly Trp Asp Asp Glu Leu Gln Lys Pro Gly Ala Gln Val
        195                 200                 205

Tyr Met His Phe Met Gln Glu His Thr Cys Tyr Asp Ala Met Ala Thr
    210                 215                 220

Ser Ser Lys Leu Val Ile Phe Asp Thr Met Leu Glu Ile Lys Lys Ala
225                 230                 235                 240

Phe Phe Ala Leu Val Ala Asn Gly Val Arg Ala Ala Pro Leu Trp Asp
                245                 250                 255

Ser Lys Lys Gln Ser Phe Val Gly Met Leu Thr Ile Thr Asp Phe Ile
            260                 265                 270

Leu Val Leu His Arg Tyr Tyr Arg Ser Pro Leu Val Gln Ile Tyr Glu
        275                 280                 285

Ile Glu Glu His Lys Ile Glu Thr Trp Arg Glu Ile Tyr Leu Gln Gly
    290                 295                 300

Cys Phe Lys Pro Leu Val Ser Ile Ser Pro Asn Asp Ser Leu Phe Glu
305                 310                 315                 320

Ala Val Tyr Ala Leu Ile Lys Asn Arg Ile His Arg Leu Pro Val Leu
                325                 330                 335

Asp Pro Val Ser Gly Ala Val Leu His Ile Leu Thr His Lys Arg Leu
            340                 345                 350
```

```
Leu Lys Phe Leu His Ile Phe Gly Thr Leu Leu Pro Arg Pro Ser Phe
        355                 360                 365

Leu Tyr Arg Thr Ile Gln Asp Leu Gly Ile Gly Thr Phe Arg Asp Leu
    370                 375                 380

Ala Val Val Leu Glu Thr Ala Pro Ile Leu Thr Ala Leu Asp Ile Phe
385                 390                 395                 400

Val Asp Arg Arg Val Ser Ala Leu Pro Val Val Asn Glu Thr Gly Gln
                405                 410                 415

Val Val Gly Leu Tyr Ser Arg Phe Asp Val Ile His Leu Ala Ala Gln
            420                 425                 430

Gln Thr Tyr Asn His Leu Asp Met Asn Val Gly Glu Ala Leu Arg Gln
        435                 440                 445

Arg Thr Leu Cys Leu Glu Gly Val Leu Ser Cys Gln Pro His Glu Thr
    450                 455                 460

Leu Gly Glu Val Ile Asp Arg Ile Val Arg Glu Gln Val His Arg Leu
465                 470                 475                 480

Val Leu Val Asp Glu Thr Gln His Leu Leu Gly Val Val Ser Leu Ser
                485                 490                 495

Asp Ile Leu Gln Ala Leu Val Leu Ser Pro Ala Gly Ile Asp Ala Leu
            500                 505                 510

Gly Ala

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ggagcaaatg tgcagacaag                                              20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
cccacgaagc tctgcttctt                                              20

<210> SEQ ID NO 35
<211> LENGTH: 16
<212> TYPE: DNA
<213> ORGANISM: Artificial Sequence
<220> FEATURE:
<223> OTHER INFORMATION: Primer

<400> SEQUENCE: 35
tggccaacgg cgtcca                                                  16

<210> SEQ ID NO 36
<211> LENGTH: 15
<212> TYPE: DNA
<213> ORGANISM: Artificial Sequence
<220> FEATURE:
<223> OTHER INFORMATION: Primer

<400> SEQUENCE: 36
```
ggccaacggc gtccg                                                        15

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
agcggcacct ttgtgaaaaa aaaaa                                             25

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
caaactcttc taggcgtgt                                                    19

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
gtttctggaa cttccatatg ccatgg                                            26

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gggaacgatt caccctcaac                                                   20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
agcccctcct cacccacgaa                                                   20

<210> SEQ ID NO 42
<211> LENGTH: 40
<212> TYPE: DNA
<213> ORGANISM: Artificial Sequence
<220> FEATURE:
<223> OTHER INFORMATION: Primer

<400> SEQUENCE: 42
aaaaaccaaa aaaccgctc agcccctcct cacccacgaa                              40

VARIANTS OF THE GAMMA CHAIN OF AMPX, DNA SEQUENCES ENCODING THE SAME, AND USES THEREOF

CROSS-REFERENCE TO RELATED APPLICATIONS

This application is a continuation of U.S. Ser. No. 10/070,794, filed on Oct. 4, 2002 now abandoned, which is a National Stage application under 35 U.S.C. § 371 and claims benefit under 35 U.S.C. § 119(a) of International Application No. PCT/EP00/09896, filed Sep. 11, 2000, which claims benefit of EP 00401388.4, filed May 18, 2000, and EP 99402236.6, filed Sep. 10, 1999.

BRIEF DESCRIPTION OF DRAWINGS

FIG. 2 is a sequence of a pig cDNA sequence (SEQ ID NO:1) having highly significant sequence similarity to various AMP-activated protein kinase γ sequences, including the yeast SNF4 sequence. 5' UTR: 5' untranslated region; 3' UTR: 3' untranslated region; CDS: coding sequence; ***: stop codon; '-': identity to master sequence; '.': alignment gap. (23:12-26)

FIG. 3 is an alignment of human (SEQ ID NO:30) and porcine (SEQ ID NO:28) PRKAG3 sequences with other AMPK γ sequences. Sequences used: HumG1: Genbank U42412; MusG1: Genbank AF036535; HumG2: Human PRKAG2 (Genbank AJ249976); PigG3: pig PRKAG3 (this study); HumG3: human PRKAG3 (this study); Dros: *Drosophila* (Genbank AF094764); SNF4 (yeast): Genbank M30470. *: stop codon; '-': identity to master sequence; '.': alignment gap. The four CBS domains are overlined and the position of the RN⁻ mutation is indicated by an arrow. (8:20-22; 24:3-24)

FIG. 6 is a series of graphs showing typical results of oligonucleotide ligation assays for the three possible genotypes of the R41Q mutation (A/A, A/G, and G/G). Genotypes were determined using DNA samples collected from 68 Swedish Hampshire animals phenotyped as either RN⁻ or rn⁺ based on their glycolytic potential value. All RN⁻ animals were scored as homozygous A/A (n=28) or heterozygous A/G (nq36) at nucleotide position 122, whereas the rn⁺ animals were homozygous G/G (n=4) at this position. (31:29-32:2).

Figure 1:
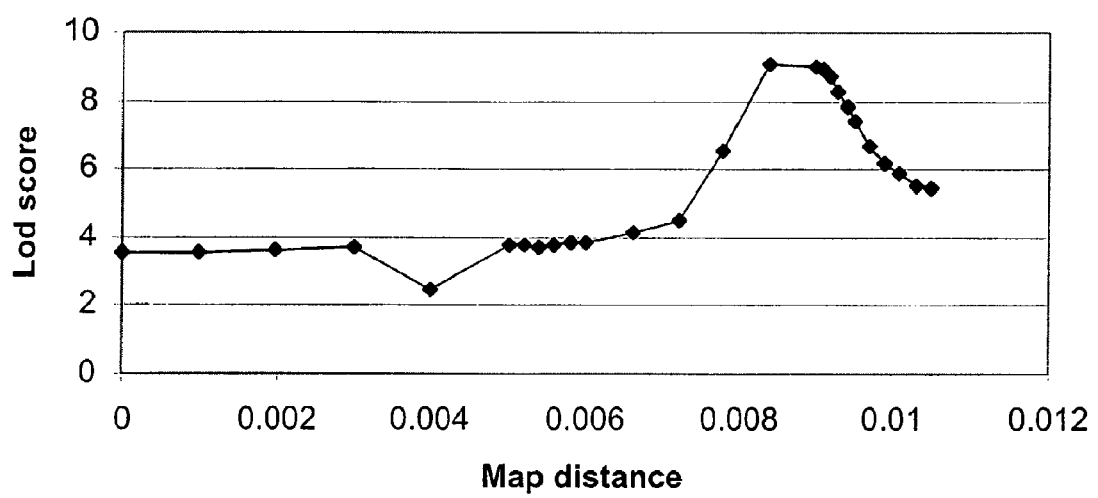
FIG. 1 shows the results of linkage disequilibrium analysis done with the markers shown in Table 1 and a random sample of 68 breeding boars from the Swedish Hampshire population, scored for the RN phenotype by measuring glycogen content in muscle. (22:11-13)

The present invention relates to new variants of the γ chain of AMP-activated protein kinase (AMPK), to genes encoding said variants and to uses thereof.

AMPK has a key role in regulating the energy metabolism in the eukaryotic cell (HARDIE et al., Annu. Rev. Biochem., 67, 821-855, 1998; KEMP et al., TIBS, 24, 22-25, 1999).

Mammalian AMPK is a heterotrimeric complex comprising a catalytic α subunit and two non-catalytic β and γ subunits that regulate the activity of the α subunit. The yeast homologue denoted SNF1) of this enzyme complex is well characterised; it comprises a catalytic chain (Snf1) corresponding to the mammalian α subunit, and regulatory subunits: Sip1, Sip2 and Gal83 correspond to the mammalian β subunit, and Snf4 correspond to the mammalian γ subunit. Sequence data show that AMPK homologues exist also in *Caenorhabditis elegans* and *Drosophila*.

It has been observed that mutations in yeast SNF1 and SNF4 cause defects in the transcription of glucose-repressed genes, sporulation, thermotolerance, peroxisome biogenesis, and glycogen storage.

In the mammalian cells, AMPK has been proposed to act as a "fuel gauge". It is activated by an increase in the AMP:ATP ratio, resulting from cellular stresses such as heat shock and depletion of glucose and ATP. Activated AMPK turns on ATP-producing pathways (e.g. fatty acid oxidisation) and inhibits ATP-consuming pathways (e.g. fatty acid and cholesterol synthesis), through phosphorylation of the enzymes acetyl-CoA carboxylase and hydroxymethylglutaryl-CoA (HMG-CoA) reductase. It has also been reported to inactivate in vitro glycogen synthase, the key regulatory enzyme of glycogen synthesis, by phosphorylation (HARDIE et al., 1998, supra); however, whether glycogen synthase is a physiological target of AMPK in vivo remained unclear.

Several isoforms of the three different AMPK subunits are present in mammals. In humans, PRKAA1 on human chromosome (HSA) 5p12 and PRKAA2 on HSA1p31 respectively encode isoforms α1 and α2 of the α subunit, PRKAB1 on HSA12q24.1 and PRKAB2 (not yet mapped) respectively encode isoforms β1 and β2 of the β subunit, and PRKAG1 on HSA12q13.1 and PRKAG2 on HSA7q35-q36 respectively encode isoforms γ1 and γ2 of the γ subunit (OMIM database, available on the World Wide Web at ncbi.nlm.nih.gov/omim, July 1999). HARDIE et al., [1998, supra] also mention the existence of a third isoform (γ3) of the γ subunit of AMPK but do not provide any information about it. Analysis of the sequences of these γ subunits shows that they are essentially composed of four cystathione β synthase (CBS) domains whose function is unknown. No phenotypic effect resulting from a mutation in either of the AMPK subunits has yet been documented.

On the other hand, it has been observed that most Hampshire pigs have a high intramuscular glycogen concentration. In these pigs, glycogenolysis which occurs after slaughtering leads to an important decrease of the pH, resulting in acid meat having a reduced water-holding capacity and giving a reduced yield of cured cooked ham.

The locus (named RN) associated with high muscular content of glycogen was first identified by family segregation analysis of phenotypic data from Hampshire pigs (LE ROY et at., Genet. Res., 55, 33-40, 1990). A fully dominant allele, RN⁻, correlated with high glycogen content occurs at a high frequency in most Hampshire populations while pigs from other breeds are assumed to be homozygous for the normal, recessive rn⁺ allele. Subsequent studies showed that RN⁻ carriers have a large increase (about 70%) of glycogen in skeletal muscle but not in liver (MONIN et al., in 38$^{th}$ ICoMST, Clermont-Ferrand, FRANCE, 1992).

The large difference in glycogen content between RN⁻ and rn⁺ pigs leads to marked differences in meat quality and technological yield (ENFÄLT et al., J. Anim. Sci., 75, 2924-2935, 1997). The RN⁻ allele is therefore of considerable economical significance in the pig industry and most breeding companies would like to reduce or eliminate this dominant mutation.

The RN phenotype can be determined by measuring the glycolytic potential in muscle biopsies from live animals, or after slaughter (MONIN et al., Meat Science, 13, 49-63, 1985). However, this method has severe limitations for application in practical breeding programs. The accuracy of the test is not 100%: as there is some overlap in the phenotypic distribution of RN⁻ and rn⁺, the test is not able to distinguish RN⁻/RN⁻ homozygotes and RN⁻/rn⁺ heterozygotes. Further, the sampling of muscle biopsies on live animals is invasive and costly.

Thus, there is a strong need for the development of a simple diagnostic DNA test for the RN locus. Moreover, the dramatic phenotypic effect of the RN gene in pigs implies that this gene has an important role in the regulation of carbohydrate metabolism in skeletal muscle in other vertebrates, in particular mammals.

Skeletal muscle and liver are the two major reservoirs of glycogen in mammals and the observation of an increased muscular glycogen while liver glycogen is normal suggests that the RN⁻ phenotype maybe due to a mutation in a gene expressed in muscle but not in liver. The inventors have previously reported that the RN gene is located on pig chromosome 15 (MILAN et al., Mamm. Genome, 7, 47-51, 1996; MARIANI et al., Mamm. Genome, 7, 52-54, 1996; LOOFT et al., Genetics Selection Evolution, 28, 437-442, 1996). They have now discovered that the RN⁻ allele is associated with a non-conservative mutation in a gene encoding a new muscle-specific isoform of the AMP-activated protein kinase (AMPK) γ chain.

The various aspects of the present invention are based upon the discovery and characterisation of this mutation and the identification and isolation of the mutant gene.

According to the invention it is shown that a mutation in a γ chain of AMPK results in an altered regulation of carbohydrate metabolism, demonstrating that AMPK is an essential component of said metabolism. It is also provided a nucleic acid sequence encoding a muscle-specific isoform of the γ chain of AMPK. Thus it is provided means to regulate carbohydrate metabolism, more specifically to detect and/or correct potential or actual dysfunctions of the regulation of carbohydrate metabolism, in particular in skeletal muscle.

The invention provides a polypeptide comprising an amino acid sequence having at least 70% identity or at least 85% similarity, preferably 80% identity or at least 90% similarity, more preferably at least 90% identity or at least 95% identity or at least 99% similarity, with the polypeptide SEQ ID NO: 2. The invention also provides an isolated nucleic acid sequence encoding said polypeptide, as well as the complement of said nucleic sequence.

Said polypeptide represents a new muscle-specific isoform of the γ chain of AMPK, and will also be hereinafter referred as PRKAG3; the gene encoding said polypeptide will also be hereinafter referred as PKAG3.

According to a preferred embodiment of the invention, said polypeptide comprises an amino acid sequence having at least 75% identity, preferably at least 80% identity with the polypeptide SEQ ID NO: 28.

"Identity" of a sequence with a reference sequence refers to the percent of residues that are the same when the two sequences are aligned for maximum correspondence between residues positions. A polypeptide having an amino acid sequence having at least X % identity with a reference sequence is defined herein as a polypeptide whose sequence may include up to 100-X amino acid alterations per each 100 amino acids of the reference amino acid sequence. Amino acids alterations include deletion, substitution or insertion of consecutive or scattered amino acid residues in the reference sequence.

"Similarity" of a sequence with a reference sequence refers to the percent of residues that are the same or only differ by conservative amino acid substitutions when the two sequences are aligned for maximum correspondence between residues positions. A conservative amino acid substitution is defined as the substitution of an amino acid residue for another amino acid residue with similar chemical properties (e.g. size, charge or polarity), which generally does not change the functional properties of the protein. A polypeptide having an amino acid sequence having at least X % similarity with a reference sequence is defined herein as a polypeptide whose sequence may include up to (100-X) non-conservative amino acid alterations per each 100 amino acids of the reference amino acid sequence. Non-conservative amino acids alterations include deletion, insertion, or non-conservative substitution of consecutive or scattered amino acid residues in the reference sequence.

For instance:
searching the "GenBank nr" database using BLASTp (ALTSCHUL et al., Nucleic Acids Res., 25, 3389-3402, 1997) with default settings and the whole sequence SEQ ID NO: 2 as a query, the higher percents of identity or similarity with SEQ ID NO: 2 were found for:

γ1 subunit of human AMPK: 65% identity or 82% similarity (score: 399);
γ1 subunit of rat AMPK: 65% identity or 82% similarity (score: 399);
γ1 subunit of murine AMPK: 64% identity or 80% similarity (score: 390);
γ subunit of *Drosophila* AMPK: 53% identity or 75% similarity (score: 332);
Yeast Snf4: 33% identity or 56% similarity (score: 173);
searching the "GenBank nr" database using BLASTp with default settings and the whole sequence SEQ ID NO: 28 as a query, the higher percents of identity or similarity were found for:
γ1 subunit of human AMPK: 64% identity or 80% similarity (score: 403);
γ2 subunit of human AMPK: 62% identity or 83% similarity (score: 425);
γ1 subunit of rat AMPK: 61% identity or 77% similarity (score: 404);
γ1 subunit of murine AMPK: 63% identity or 79% similarity (score: 394);
γ subunit of *Drosophila* AMPK: 52% identity or 76% similarity (score: 340).

Polypeptides of the invention include for instance any polypeptide (whether natural, synthetic, semi-synthetic, or recombinant) from any vertebrate species, more specifically from birds, such as poultry, or mammals, including bovine, ovine, porcine, murine, equine, and human, and comprising, or consisting of, the amino acid sequence of either:
a functional PRKAG3; or
a functionally altered mutant of PRKAG3.

"Functional" refers to a protein having a normal biological activity. Such a protein may comprise silent mutations inducing no substantial change in its activity, and having no noticeable phenotypic effects. Non-limitative examples of functional PRKAG3 are:
a porcine PRKAG3 comprising at least the sequence represented in the enclosed sequence listing under SEQ ID NO: 2; this includes, for instance the polypeptide SEQ ID NO: 28;

a human PRKAG3 comprising at least the sequence represented in the enclosed sequence listing under SEQ ID NO: 4; this include for instance the polypeptide SEQ ID NO: 30.

The invention also includes splice variants of PRKAG3: for instance, the nucleotide sequence SEQ ID NO: 27, and the corresponding amino-acid sequence SEQ ID NO: 28 on one hand, and the nucleotide sequence SEQ ID NO: 31 and the corresponding amino-acid sequence SEQ ID NO: 32 on the other hand represent two different splice variants or porcine PRKAG3.

A "functionally altered mutant" of a protein comprises one or several mutations inducing a change in its activity. Such mutations include in particular deletions, insertions, or substitutions of amino acid residues in a domain essential for the biological activity of said protein. They may result for instance in a partial or total loss of activity, or conversely in an increase of activity, or in an impairment of the response to regulatory effectors. Deletions, insertions, or non-conservative substitutions are more likely to result in a critical effect on the biological activity; however conservative substitutions may also induce a noticeable effect, if they occur at an important position of an active site of the protein.

Non-limitative examples of functionally altered mutants of PRKAG3 are:

the R41Q variant resulting from the non-conservative substitution of an arginine residue in position 41 of SEQ ID NO: 2 or SEQ ID NO: 4 by a glutamine residue (this substitution results in an important increase of the glycogen content, inducing an increased glycolytic potential of the skeletal muscle);

the V40I variant resulting from the substitution of a valine residue in position 40 of SEQ ID NO: 2 or SEQ ID NO: 4 by an isoleucine residue (this substitution results in a decrease of the glycogen content and thus of the glycolytic potential of the skeletal muscle).

These substitutions occur inside a portion of the first CBS domain that is highly conserved between PRKAG3 and the previously known isoforms of the γ subunit of AMPK.

Residue numbers for PRKAG3 refer to the amino acid numbering of SEQ ID NO: 2 or SEQ ID NO: 4. Alignment of human and porcine PRKAG3 sequences with previously known γ1 and γ2 isoforms is shown in FIG. 3.

The invention also provides mutants of PRKAG3 which may for instance be obtained by deletion of part of a PRKAG3 polypeptide. Said mutants are generally functionally altered. They may have identity with the overall PRKAG3 sequence lower than 70%. However, the identity of the non-deleted sequences of said mutants, when aligned with the corresponding PRKAG3 sequences and more specifically with the corresponding sequences from SEQ ID NO: 2, should remain higher than 70%. Said mutants may for instance result from the expression of nucleic acid sequences obtained by deletion or insertion of a nucleic acid segment, or by a punctual mutation introducing a nonsense codon; in a nucleic acid sequence encoding a functional PRKAG3.

The invention also provides a functionally altered mutant of a γ subunit of AMPK, wherein said mutant comprises at least one mutation responsible for said functional alteration located within the first CBS domain, and preferably within the region thereof aligned with the region spanning from residue 30 to residue 50 of SEQ ID NO: 2 or SEQ ID NO: 4. Said mutation may result from the insertion, deletion, and/or substitution of one amino-acid or of several amino-acids, adjacent or not. More preferably the mutation is located within the region aligned with the region spanning from residue 35 to residue 45 of SEQ ID NO: 2 or SEQ ID NO: 4, for instance within the region spanning from residue 65 to residue 75 of the γ1 isoform.

According to a particular embodiment, said mutation is a non-conservative substitution, preferably a R→Q substitution. According to another particular embodiment, said mutation is a conservative substitution, preferably a V→I substitution.

Advantageously, the mutation is located at a residue corresponding to residue 41 of SEQ ID NO: 2 or SEQ ID NO: 4, for instance in the case of the γ1 isoform, at residue 70, or at a residue corresponding to residue 40 of SEQ ID NO: 2 or SEQ ID NO: 4, for instance in the case of the γ1 isoform, at residue 69.

The invention also provides a heterotrimeric AMPK wherein the γ subunit consists of a polypeptide of the invention.

The invention also provides isolated nucleic acid sequences encoding any of the above-defined functional or functionally altered PRKAG3 or functionally altered mutants of the γ subunit of AMPK, and nucleic acid sequences complementary of any one of these nucleic acid sequences.

This includes particularly any isolated nucleic acid having the sequence of any of the naturally occurring alleles of a PRKAG3 gene, as well as any isolated nucleic acid having the sequence of an artificial mutant of a PRKAG3 gene, provided that said nucleic acid does not consist of the EST GENBANK AA178898.

This also includes any isolated nucleic acid having the sequence of a natural or artificial mutant of a PRKAG1 or a PRKAG2 gene, wherein said mutant encodes a functionally altered γ1 or γ2 subunit of the AMPK as defined above.

Nucleic acids of the invention may be obtained by the well-known methods of recombinant DNA technology and/or of chemical DNA synthesis. These methods also allow to introduce the desired mutations in a naturally occurring DNA sequence.

Examples of the nucleic acids encoding naturally occurring alleles of a PRKAG3 gene are represented by SEQ ID NO: 1, which encodes a naturally occurring allele of the porcine gene and SEQ ID NO: 3, which encodes a naturally occurring allele of the human gene. These sequences may be used to generate probes allowing the isolation of PRKAG3 from other species or of other allelic forms of PRKAG3 from a same species, by screening a library of genomic DNA or of cDNA.

The invention also includes genomic DNA sequences from any vertebrate species, more specifically from birds, such as poultry, or mammals, including in particular bovine, ovine, porcine, murine, equine, and human, comprising at least a portion of a nucleic acid sequence encoding a polypeptide of the invention, preferably a portion of a PRKAG3 gene, and up to 500 kb, preferably up to 100 kb of a 3' and/or of a 5' adjacent genomic sequence.

Such genomic DNA sequences may be obtained by methods known in the art, for instance by extension of a nucleic acid sequence encoding a polypeptide of the invention, employing a method such as restriction-site PCR (SARKAR et al., PCR Methods Applic., 2, 318-322, 1993), inverse PCR (TRIGLIA et al., Nucleic Acids Res., 16, 8186, 1988) using divergent primers based on a PRKAG3 coding region, capture PCR (LAGERSTROM et al., PCR Methods Applic., 1, 111-119, 1991), or the like.

The invention also includes specific fragments of a nucleic acid sequence encoding a polypeptide of the invention, or of a genomic DNA sequence of the invention as well as nucleic acid fragments specifically hybridising therewith. Preferably these fragments are at least 15 bp long, more preferably at least 20 bp long.

"Specific fragments" refers to nucleic acid fragments having a sequence that is found only in the nucleic acids sequences encoding a polypeptide of the invention, and is not found in nucleic acids sequences encoding related polypeptides of the prior art. This excludes the nucleic acid fragments that consist of a sequence shared with one of the known PRKAG1 or PRKAG2 genes.

"Specifically hybridising fragments" refers to nucleic acid fragments which can hybridise, under stringent conditions, only with nucleic acid sequences encoding a polypeptide of the invention, without hybridising with nucleic acid sequences encoding related polypeptides of the prior art. This excludes the nucleic acid fragments that consist of the complement of a sequence with one of the known PRKAG1 and PRKAG2 genes.

Nucleic acid fragments that consist of the EST GENBANK AA178898 or the EST GENBANK W94830 or the complements thereof are also excluded.

Said specific or specifically hybridising nucleic acid fragments may for example be used as primers or probes for detecting and/or amplifying a nucleic acid sequence encoding a polypeptide of the invention. The invention encompasses set of primers comprising at least one primer consisting of a specific or specifically hybridising nucleic acid fragment as defined above.

The invention also provides recombinant vectors comprising a nucleic acid sequence encoding a polypeptide of the invention. Vectors of the invention are preferably expression vectors, wherein a sequence encoding a polypeptide of the invention is placed under control of appropriate transcriptional and translational control elements. These vectors may be obtained and introduced in a host cell by the well-known recombinant DNA and genetic engineering techniques.

The invention also comprises a prokaryotic or eukaryotic host cell transformed by a vector of the invention, preferably an expression vector.

A polypeptide of the invention may be obtained by culturing the host cell containing an expression vector comprising a nucleic acid sequence encoding said polypeptide, under conditions suitable for the expression of the polypeptide, and recovering the polypeptide from the host cell culture.

A heterotrimeric AMPK wherein the γ subunit consists of a polypeptide of the invention may be obtained by expressing, together or separately, a nucleic acid sequence encoding a polypeptide of the invention, a nucleic acid sequence an α subunit, and a nucleic acid sequence encoding β subunit, and reconstituting the heterotrimer.

The polypeptides thus obtained, or immunogenic fragments thereof may be used to prepare antibodies, employing methods well known in the art. Antibodies directed against the whole PRKAG3 polypeptide and able to recognise any variant thereof may thus be obtained. Antibodies directed against a specific epitope of a particular variant (functional or not) of PRKAG3 or antibodies directed against a specific epitope of a functionally altered mutant having a mutation in the first CBS domain of a γ subunit of AMPK, and able to recognise said variant or functionally altered mutant may also be obtained.

As shown herein, mutations in a γ subunit of AMPK, and particularly mutations in the first CBS domain of a γ subunit of AMPK are likely to cause disorders in the energy metabolism (e.g. diabetes, obesity) in vertebrates, including humans. Further, mutations in the first CBS domain or other parts of the PRKAG3 gene are likely to cause disorders in the muscular metabolism leading to diseases such as myopathy, diabetes and cardiovascular diseases.

The present invention provides means for detecting and correcting said disorders.

More specifically, the present invention is directed to methods that utilise the nucleic acid sequences and/or polypeptidic sequences of the invention for the diagnostic evaluation, genetic testing and prognosis of a metabolic disorder.

For example, the invention provides methods for diagnosing of metabolic disorders, more specifically carbohydrate metabolism disorders, and preferably disorders correlated with an altered, in particular an excessive, glycogen accumulation in the cells, resulting from a mutation in a gene encoding a γ subunit of AMPK, wherein said methods comprise detecting and/or measuring the expression of a functionally altered PRKAG3 gene, or of a functionally altered mutant of a γ subunit of AMPK having a mutation within the first CBS domain in a nucleic acid sample obtained from a vertebrate, or detecting a mutation in the PRKAG3 gene or in a sequence encoding the first CBS domain of a γ subunit of AMPK in the genome of a vertebrate suspected of having such a disorder.

According to a preferred embodiment of the invention, the disorder is correlated with an altered, in particular an excessive, glycogen accumulation in the muscular cells and results from the expression of a functionally altered PRKAG3 gene.

The expression of a functionally altered Prkag3, or of a functionally altered mutant of a γ subunit of AMPK having a mutation within the first CBS domain may be detected or measured using either polyclonal or monoclonal antibodies specific for the functionally altered polypeptides of the invention, as defined above. Appropriate methods are known in the art. They include for instance enzyme-linked immunosorbent assay (ELISA), radioimmunoassay (RIA), and fluorescence activated cell sorting (FACS).

The nucleotide sequences of the invention may be used for detecting mutations in the PRKAG3 gene or in a sequence encoding the first CBS domain of a γ subunit of AMPK, by detection of differences in gene sequences or in adjacent sequences between normal, carrier, or affected individuals.

The invention provides a process for detecting a mutation in the PRKAG3 gene or in a sequence encoding the first CBS domain of a γ subunit of AMPK wherein said process comprises:

obtaining a nucleic acid sample from vertebrate;

checking the presence is said nucleic acid sample of a nucleic acid sequence encoding a mutant Prkag3, or a mutant of a γ subunit of AMPK having a mutation within the first CBS domain, as defined above.

According to a preferred embodiment of the invention there is provided a method for detecting a nucleic acid sequence comprising a mutation in the PRKAG3 gene or in a sequence encoding the first CBS domain of a γ subunit of AMPK wherein said process comprises:

obtaining a nucleic acid sample from a vertebrate;

contacting said nucleic acid sample with a nucleic acid probe obtained from a nucleic acid of the invention and spanning said mutation, under conditions of specific hybridisation between said probe and the mutant sequence to be detected;

detecting the hybridisation complex.

Preferably, the process of the invention further comprises, prior to hybridisation, PCR amplification from the nucleic acid sample, of a sequence comprising at least the portion of the PRKAG3 sequence or the sequence encoding the first CBS domain of the γ subunit of AMPK wherein the mutation is to be detected.

Methods allowing the specific hybridisation of a probe only with a perfectly matching complementary sequence, and useful for the detection of punctual mutations are known in the art. They include for instance Allele Specific PCR (GIBBS, Nucleic Acid Res., 17, 2427-2448, 1989), Allele Specific Oligonucleotide Screening (SAIKI et al., Nature, 324, 163-166, 1986), and the like.

A mutation in the PRKAG3 gene may also be detected through detection of polymorphic markers closely link to said mutation.

The invention also provides means for identifying said polymorphic markers, and more specifically polymorphic markers comprised within a genomic DNA sequence comprising at least a portion of a PRKAG3 gene, and up to 500 kb, preferably 300 kb, more preferably up to 100 kb of a 3' and/or of a 5' adjacent sequence.

Said polymorphic markers may be obtained for instance, by screening a genomic DNA library from a vertebrate with a probe specific for the PRKAG3 gene, in order to select clones comprising said nucleic acid sequence and flanking chromosomal sequences, and identifying a polymorphic marker in said flanking chromosomal sequences. The allele(s) of a polymorphic marker associated with a given mutant allele of the PRKAG3 gene may also easily be identified by use of a genomic DNA library from an individual wherein the presence of said mutant allele has previously been detected by hybridisation with a nucleic acid probe of the invention.

Polymorphic markers include for instance, single nucleotide polymorphisms (SNP), microsatellites, insertion/deletion polymorphism and restriction fragment length polymorphism (RFLP). These polymorphic markers may be identified by comparison of sequences flanking the PRKAG3 gene obtained from several individuals. Microsatellites may also be identified by hybridisation with a nucleic acid probe specific of known microsatellite motifs.

Once a polymorphic marker has been identified, a DNA segment spanning the polymorphic locus may be sequenced and a set of primers allowing amplification of said DNA segment may be designed.

The invention also encompasses said DNA primers.

Detection of a mutation in the PRKAG3 gene may be performed by obtaining a sample of genomic DNA from a vertebrate, amplifying a segment of said DNA spanning a polymorphic marker by polymerase chain reaction using a set of primers of the invention, and detecting in said amplified DNA the presence of an allele of said polymorphic marker associated with said mutation.

By way of example, polymorphic markers which may be obtained according to the invention, and DNA primers allowing the detection of polymorphic markers closely linked to the RN⁻ allele of porcine PRKAG3 gene are listed in Table 1 hereinafter.

According to a preferred embodiment of the invention, the vertebrate is a mammal, preferably a farm animal and more preferably a porcine, and the mutation to be detected produces a functionally altered PRKAG3. The detection of said mutation allows to predict whether said mammal or the progeny thereof is likely to have an intramuscular glycogen concentration higher or lower than the average. An example of such a mutation produces a functionally altered PRKAG3 having a R41Q substitution, and resulting in an increased glycogen content in the skeletal muscle.

Another example of such a mutation produces a functionally altered PRKAG3 having a V40I substitution, and resulting in a decreased glycogen content in the skeletal muscle. In farm animals having such a mutation, glycogenolysis which occurs after slaughtering is less important than in normal animals, resulting in a higher pH and in a potential better quality of meat.

The present invention also includes kits for the practice of the methods of the invention. The kits comprise any container which contains at least one specific fragment of a nucleic acid sequence of the invention, or at least one nucleic acid fragment able to specifically hybridise with a nucleic acid sequence of the invention. Said nucleic acid fragment may be labeled. The kits may also comprise a set of primers of the invention. They may be used in conjunction with commercially available amplification kits. They may also include positive or negative control reactions or markers, molecular weight size markers for gel electrophoresis, and the like.

Other kits of the invention may include antibodies of the invention, optionally labeled, as well as the appropriate reagents for detecting an antigen-antibody reaction. They may also include positive or negative control reactions or markers.

The invention further provides means for modulating the expression of vertebrate genes encoding a γ subunit of AMPK, and more specifically of the PRKAG3 gene and/or the synthesis or activity of the products of said genes.

A purified AMPK heterotrimer comprising wild-type or mutant PRKAG3 subunit, or a functionally altered mutant γ subunit having a mutation in the first CBS domain, may be used for screening in vitro compounds able to modulate AMPK activity, or to restore altered AMPK activity. This may be done, for instance, by:

measuring the binding of the compound to said heterotrimer, using for example high-throughput screening methods; or, measuring changes in AMPK kinase activity, using for example high-throughput screening methods.

High throughput screening methods are disclosed, for instance, in "High throughput screening: The Discovery of Bioactive Substances", J. P. DEVLIN (Ed), MARCEL DEKKER Inc., New York (1997).

Nucleic acids of the invention may be used for therapeutic purposes. For instance, complementary molecules or fragments thereof (antisense oligonucleotides) may be used to modulate AMPK activity, more specifically in muscular tissue.

Also, a nucleic acid sequence encoding a functional Prkag3 may be used for restoring a normal AMPK function.

Transformed cells or animal tissues expressing a wild-type or mutant PRKAG3, or a functionally altered mutant of a γ subunit of AMPK as defined above, or expressing an AMPK comprising said mutant Prkag3, or said functionally altered mutant of a γ subunit of AMPK, may be used as in vitro model for elucidating the mechanism of AMPK activity or for screening compounds able to modulate the expression of AMPK.

The screening may be performed by adding the compound to be tested to the culture medium of said cells or said tissues, and measuring alterations in energy metabolism in said cells or said tissues using methods such as measurements of glucose concentrations (levels), glucose uptake, or changes of the ATP/AMP ratio, glycogen or lipid/protein content.

The invention provides animals transformed with a nucleic acid sequence of the invention.

In one embodiment, said animals are transgenic animals having at least a transgene comprising a nucleic acid of the invention.

In another embodiment, said animals are knockout animals. "Knockout animals" refers to animals whose native or endogenous PRKAG3 alleles have been inactivated and which produce no functional Prkag3 of their own.

In light of the disclosure of the invention of DNA sequences encoding a wild-type or mutant Prkag3, or a functionally altered mutant of a γ subunit of AMPK, transgenic animals as well as knockout animals may be produced in accordance with techniques known in the art, for instance by means of in vivo homologous recombination.

Suitable methods for the preparation of transgenic or knock-out animals are for instance disclosed in: *Manipulating the Mouse Embryo*, 2nd Ed., by HOGAN et al., Cold Spring Harbor Laboratory Press, 1994; *Transgenic Animal Technology*, edited by C. PINKERT, Academic Press Inc., 1994; *Gene Targeting: A Practical Approach*, edited by A. L. JOYNER, Oxford University Press, 1995; *Strategies in Transgenic Animal Science*, edited by G. M. MONASTERSKY and J. M. ROBL, ASM Press, 1995; *Mouse Genetics: Concepts and Applications*, by Lee M. SILVER, Oxford University Press, 1995.

These animals may be used as models for metabolic diseases and disorders, more specifically for diseases and disorders of glycogen metabolism in muscle. For instance they may be used for screening test molecules. Transgenic animals may thus be used for screening compounds able to modulate AMPK activity. Knockout animals of the invention may be used, in particular, for screening compounds able to modulate energy metabolism, more specifically carbohydrate metabolism, in the absence of functional PRKAG3.

The screening may be performed by administering the compound to be tested to the animal, and measuring alterations in energy metabolism in said animal using methods such as glucose tolerance tests, measurements of insulin levels in blood, changes of the ATP/AMP ratio, glycogen or lipid/protein content in tissues and cells.

Transgenic or knock-out farm animals with modified meat characteristics or modified energy metabolism may also be obtained.

The present invention will be further illustrated by the additional description which follows, which refers to examples of obtention and use of nucleic acids of the invention. It should be understood however that these examples are given only by way of illustration of the invention and do not constitute in any way a limitation thereof.

EXAMPLE 1

Isolating the PRKAG3 Gene

We have screened a porcine Bacterial Artificial Chromosome (BAC) library (ROGEL-GAILLARD et al., Cytogenet and Cell Genet, 851, 273-278, 1999) and constructed a contig of overlapping BAC clones across the region of pig chromosome 15 harbouring the RN gene. These BAC clones were in turn used to develop new genetic markers in the form of single nucleotide polymorphisms (SNPs) or microsatellites (MS) as described in Table 1 below.

TABLE 1

| | Name of marker | BAC clone | Primer sequences | Size of PCR product (bp) | Marker type[a] | Alleles[b] |
|---|---|---|---|---|---|---|
| 1 | H3 | 115B9, 156E6, 361B4, 90A9 | F; 5'-GGAATTTCAAGTCAGCCAAC-3' (SEQ ID NO:5) R; 5'-CTTCAAAAGACCGTGCTACT-3' (SEQ ID NO:6) | 114-138 | MS | 114, 126, 128, 132*, 134*, 136 138 |
| 2 | MS982H1 | 982H11 | F; 5'-CTGGGAACCTCTATATGCTG-3' (SEQ ID NO:7) R; 5'-TAGGGAAATACAAATCACAG-3' (SEQ ID NO:8) | 114-157 | MS | 114, 140, 142*, 144, 146, 150, 158 |
| 3 | MS479L3 | 479L3, 297D7, 852B5, 153B5 | F; 5'-CTCCAGCTCACAGGATGACA-3' (SEQ ID NO:9) R; 5'-GTTTCTGCAGCTTTAGCATCTATTCC-3' (SEQ ID NO:10) | 150-164 | MS | 150*, 160, 162, 164 |
| 4 | MS997M35 | 997F12 | F; 5'-GAAGTATCCTGGGCTTCTGA-3' (SEQ ID NO:11) R; 5'-GTTTCTCCAGGTTTCCAGACATCCAC-3' (SEQ ID NO:12) | 138-160 | MS | 138, 144, 152, 154, 160* |
| 5 | MS482H65 | 482E7 | F; 5'-GCTTCTGTCTGCCCCTACTT-3' (SEQ ID NO:13) R; 5'-GTTTCTAAGTTCTACTGTAAGACACC-3' (SEQ ID NO:14) | 78-90 | MS | 78, 80, 88*, 90 |
| 6 | MS337H2 | 808G10, 947E5, 337G11 | F; 5'-CCAAGCTGTGGTGGCTGAAT-3' (SEQ ID NO:15) R; 5'-CAGCACAGCAGTGCCACCTA-3' (SEQ ID NO:16) | 145-165 | MS | 145, 149, 155, 161*, 165* |
| 7 | MS127B1 | 127G6, 134C9 | F; 5'-CAAACTCTTCTAGGCGTGT-3' (SEQ ID NO:17) R; 5'-GTITCTGGAACTTCCATATGCCATGG-3' (SEQ ID NO:18) | 94-108 | MS | 94, 100, 108*, 114 |
| 8 | CMKAR2 | 128A3, 37G11, 808G10, | F; 5'-AGGGTGGATGGTAGGCTTCA-3' (SEQ ID NO:19) R; 5'-GTCTCGCTCCTGAAGGAAGT-3' | 208 | SNP | 112A*, 112T; 158A*, 158G 176A*, 176G |

TABLE 1-continued

| Name of marker | BAC clone | Primer sequences | Size of PCR product (bp) | Marker type[a] | Alleles[b] |
|---|---|---|---|---|---|
| | 947E7, 1110H12 | (SEQ ID NO:20) | | | |
| 9  127G63 | 127G6, 134C9, 170D7, 1030A5, | F; 5'-AGTCACGTGGCCATGCTATC-3' (SEQ ID NO:21) R; 5'-CTCAACTGGATTGAGTCAGT-3' (SEQ ID NO:22) | 409 | SNP | 234A*, 234C |
| 10 VIL1 | 1088F2 | F; 5'-TTGGCGCAACTGTTATTTCT-3' (SEQ ID NO:23) R; 5'-AGGCAAAGGAAGAGCACAG-3' (SEQ ID NO:24) | 270 | SNP | 90T, 90G, 120A, 120G, 166C, 166T |
| 11 NRAMP1 | 315F7, 530A6, 651C12, 1088F2, 1095H3 | F; 5'-AGCCGTGGGCATCGTTGG-3' (SEQ ID NO:25) R; 5'-AGAAGGAGACAGACAGGGCGA-3' (SEQ ID NO:26) | 1300 | RFLP (StyI) | 1: 100 + 1200 bp 2: 100 + 200 + 1000 bp |

[a]MS = microsatellite; SNP = nucleotide polymorphism.
[b]Microsatellite alleles are designated according to the length of the amplified fragment while SNPs are denoted according to the polymorphic nucleotide. Alleles associated with the RN allele are marked with an asterisk.

The new markers were used together with some previously described markers to construct a high-resolution linkage map. Standard linkage analysis using pedigree data comprising about 1,000 informative meioses for segregation at the RN locus made it possible to exclude RN from the region proximal to MS479L3 and distal to microsatellite Sw936. Linkage Disequilibrium (LD) analysis was done with the same markers and a random sample of 68 breeding boars from the Swedish Hampshire population, scored for the RN phenotype by measuring glycogen content in muscle. The results of LD analysis using the DISMULT program (TERWILLIGER, Am. J. Hum. Genet., 56, 777-787, 1995) are shown in FIG. 1. They reveal a sharp LD peak around the markers MS127B1 and SNP127G63. These markers appeared to show complete linkage disequilibrium with the RN⁻ allele, i.e., RN⁻ was associated with a single allele at these two loci. The most simple interpretation of this finding is that the RN⁻ mutation arose on a chromosome carrying these alleles and that the two markers are so closely linked to the RN locus that the recombination frequency is close to 0%. The two markers are both present on the overlapping BAC clones 127G6 and 134C9 suggesting that the RN gene may reside on the same clone or one of the neighbouring clones.

A short-gun library of the BAC clone 127G6 was constructed and more than 1,000 sequence reads were collected giving about 500,000 base pair random DNA sequence from the clone. The data were analysed and sequence contigs constructed with the PHRED, PHRAP and CONSED software package (University of Washington Genome Center, available online at bozeman.mbt.washington.edu). The sequence data were masked for repeats using the REPEATMASKER software (available online at ftp.genome.washington.edu/cgi.bin/RepeatMasker) and BLAST searches were carried out using the NCBI web site (available on the World Wide Web at ncbi.nlm.nih.gov). Three convincing matches to coding sequences were obtained. Two of these were against human cDNA sequences/genes, KIAA0173 described as being similar to pig tubulin-tyrosine ligase and located on HSA2q (UniGene cluster Hs. 169910, available on the World Wide Web at ncbi.nlm.nih.gov/UniGene) and CYP27A1 located on HSA2q33-ter (UniGene cluster Hs. 82568). The results strongly suggested that the pig coding sequences are orthologous to these human genes as it is well established that the RN region is homologous to HASA2q33-36 (ROBIC et al., Mamm. Genome, 10, 565-568, 1999). However, none of these sequences appeared as plausible candidate genes for RN. The third coding sequence identified in BAC 127G6 showed highly significant sequence similarity to various AMP-activated protein kinase γ sequences including the yeast SNF4 sequence. The cDNA sequence of this gene was determined by RT-PCR and RACE analysis using muscle mRNA from an rn⁺/rn⁺ homozygote. This sequence is shown in FIG. 2 and in the enclosed sequence listing under SEQ ID NO:1.

Legend of FIG. 2:
5' UTR: 5' untranslated region
3' UTR: 3' untranslated region
CDS coding sequence
***: stop codon
'-': identity to master sequence
'.': alignment gap The frame of translation was determined on the basis of homology to other members in the protein family and assuming that the first methionine codon in frame is the start codon. The polypeptidic sequence deduced on this basis is shown in the enclosed sequence listing under SEQ ID NO:2.

The complete nucleotidic sequence of pig PRKAG3 cDNA is shown in the enclosed sequence listing under SEQ ID NO:27 and the complete polypeptidic sequence is shown in the enclosed sequence listing under SEQ ID NO:28 and in FIG. 3.

FIG. 3 shows an amino acid alignment constructed with the CLUSTAL W program (THOMPSON et al., Nucleic Acids Research, 22, 4673-4680, 1994) with representative AMPK γ sequences in the nucleotide databases.

Legend of FIG. 3:
Sequences used:
HumG1: Genbank U42412
MusG1: Genbank AF036535
HumG2: Human PRKAG2 (Genbank AJ249976)

PigG3: pig PRKAG3 (this study)
HumG3: human PRKAG3 (this study)
Dros: *Drosophila* (Genbank AF094764)
SNF4 (yeast): Genbank M30470

Both the PRKAG2 and *Drosophila* sequences have longer aminoterminal regions but they do not show significant homology to the aminoterminal region of PRKAG3 and were not included.

Abbreviations:
*: stop codon
'-': identity to master sequence
'.': alignment gap The four CBS domains are overlined and the position of the RN⁻ mutation is indicated by an arrow.

Table 2 below shows the amino acid (above diagonal) and nucleotide sequence (below diagonal) identities (in %) among mammalian, *Drosophila* and yeast AMPKG/SNF4 sequences. In the case of pig PRKAG3 and human PRKAG3, the identities were calculated referring to the portions thereof represented respectively by SEQ ID NO:1 and SEQ ID NO:3, for the nucleotide sequences, and by SEQ ID NO:2 and SEQ ID NO:4, for the amino acid sequences.

TABLE 2

|       | PigG3 | HumG3 | HumG1 | RatG1 | MusG1 | HumG2 | Dros | SNF4 |
|-------|-------|-------|-------|-------|-------|-------|------|------|
| PigG3 | —     | 97.0  | 64.2  | 64.2  | 63.9  | 62.6  | 53.2 | 34.0 |
| HumG3 | 90.7  | —     | 63.6  | 63.6  | 63.6  | 62.6  | 53.5 | 34.4 |
| HumG1 | 64.2  | 64.5  | —     | 96.7  | 96.3  | 75.6  | 60.9 | 33.5 |
| RatG1 | 65.8  | 65.8  | 88.0  | —     | 97.4  | 75.3  | 61.1 | 33.5 |
| MusG1 | 65.3  | 64.8  | 87.2  | 92.8  | —     | 74.6  | 61.7 | 33.5 |
| HumG2 | 61.6  | 61.6  | 68.1  | 67.8  | 65.9  | —     | 63.1 | 34.5 |
| Dros  | 58.4  | 58.4  | 59.0  | 59.3  | 59.0  | 60.0  | —    | 36.2 |
| SNF4  | 44.0  | 44.2  | 45.4  | 44.6  | 45.3  | 45.7  | 44.8 | —    |

Figure 4:
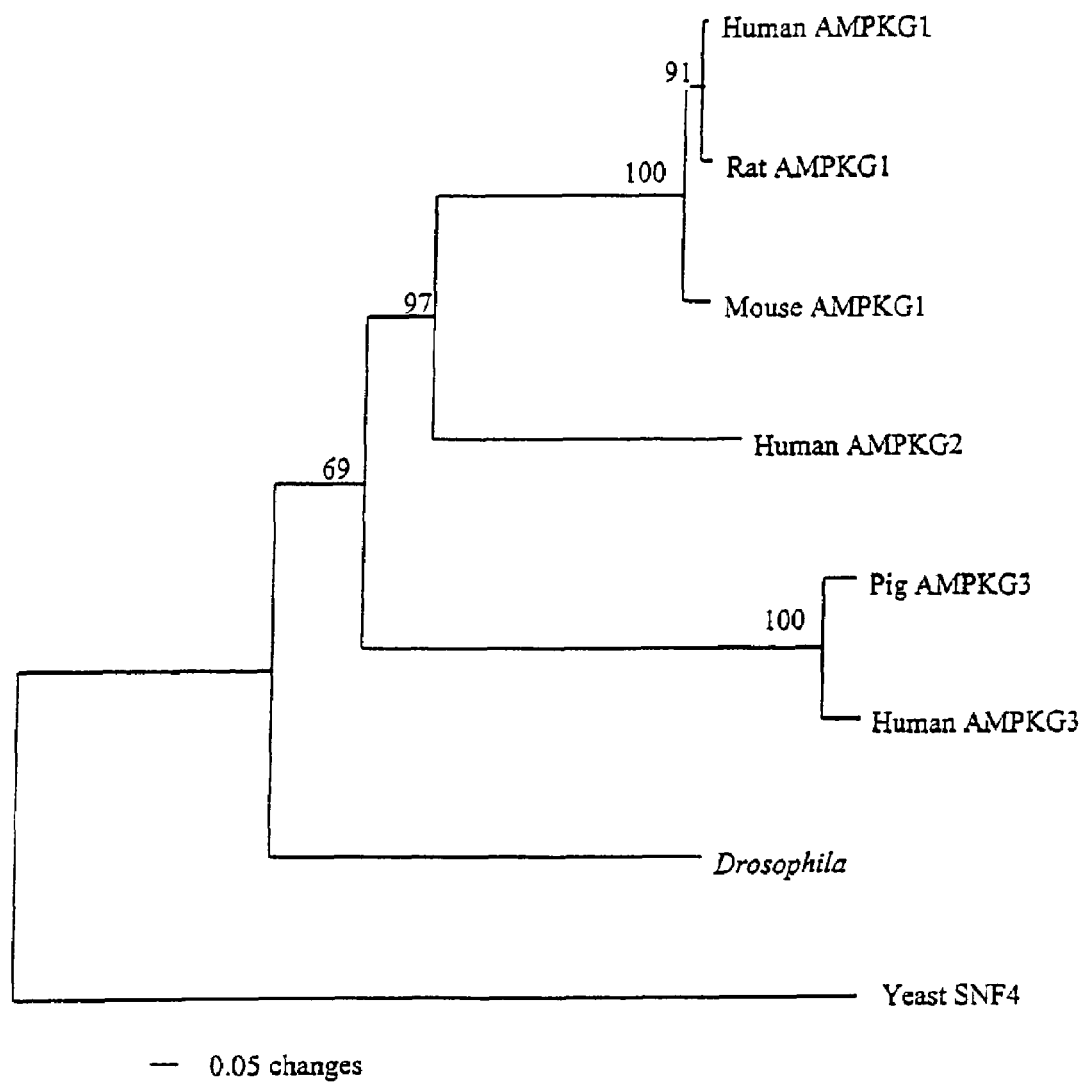
FIG. 4 shows a Neighbor-Joining phylogenetic tree constructed using yeast SNF4 as outgroup; support for branch orders obtained in bootstrap analysis with 1,000 replicates are indicated, and the scale of the tree is indicated at the bottom. (25:2-9)

FIG. 4 shows a Neighbor-Joining phylogenetic tree constructed with the PAUP software (SWOFFORD, *Phylogenetic analysis using parsimony (and other methods)*, Sinauer Associates, Inc. Publishers Sunderland, Massachusetts, 1998) using yeast SNF4 as outgroup; support for branch orders obtained in bootstrap analysis with 1,000 replicates are indicated, scales of tree is indicated at the bottom. The result showed that the pig gene located in the RN region is distinct from mammalian PRKAG1 AND PRKAG2 isoforms and most likely orthologous to a human gene represented by the human EST sequence AA178898 (GenBank) derived from a muscle cDNA library. This gene is herein denoted PRKAG3 since it is the third isoform of a mammalian AMP-activated protein kinase γ characterised so far.

The cDNA sequence of this gene was determined by RT-PCR and 5' RACE analysis using human skeletal muscle cDNA (Clontech, Palo Alto, Calif.). This sequence is shown in FIG. 2 and in the sequence listing under SEQ ID NO:3. The deduced polypeptidic sequence having 97% identity with the porcine sequence SEQ ID NO:2 (cf. Table 2) is shown on FIG. 2 and in the sequence listing under SEQ ID NO:4.

The complete cDNA sequence is also shown in the enclosed sequence listing under SEQ ID NO:29; the deduced polypeptidic sequence is shown in the enclosed sequence listing under SEQ ID NO:30 and in FIG. 3.

Using the high resolution human TNG radiation hybrid panel: (available online at shgc-www.stanford.edu/RH/TNG-index.html) we mapped the human homologs of PRKAG3, CYP27A1 and KIAA0173, all present in the porcine BAC127G6. The three genes are also very closely linked in the human genome. PRKAG3 was mapped at a distance of 33 $cR_{50,000}$ from KIAA0173 and 52 $cR_{50,00}$ from CYP27A1, with lod score support of 6.8 and 4.5, respectively.

The established role of AMPX in regulating energy metabolism, including glycogen storage, and its location in the region showing maximum linkage disequilibrium made PRKAG3 a very strong candidate gene for RN. This was further strengthened by hybridisation analysis of a human multiple tissue northern blots (CLONTECH, Palo Alto, Calif.) using human PRKAG1 (IMAGE clone 0362755 corresponding to GenBank entry AA018675), human PRKAG2 (IMAGE clone 0322735 corresponding to GenBank entry W15439) and a porcine PRKAG3 probe. The results are shown in FIG. 5.

Figure 5:
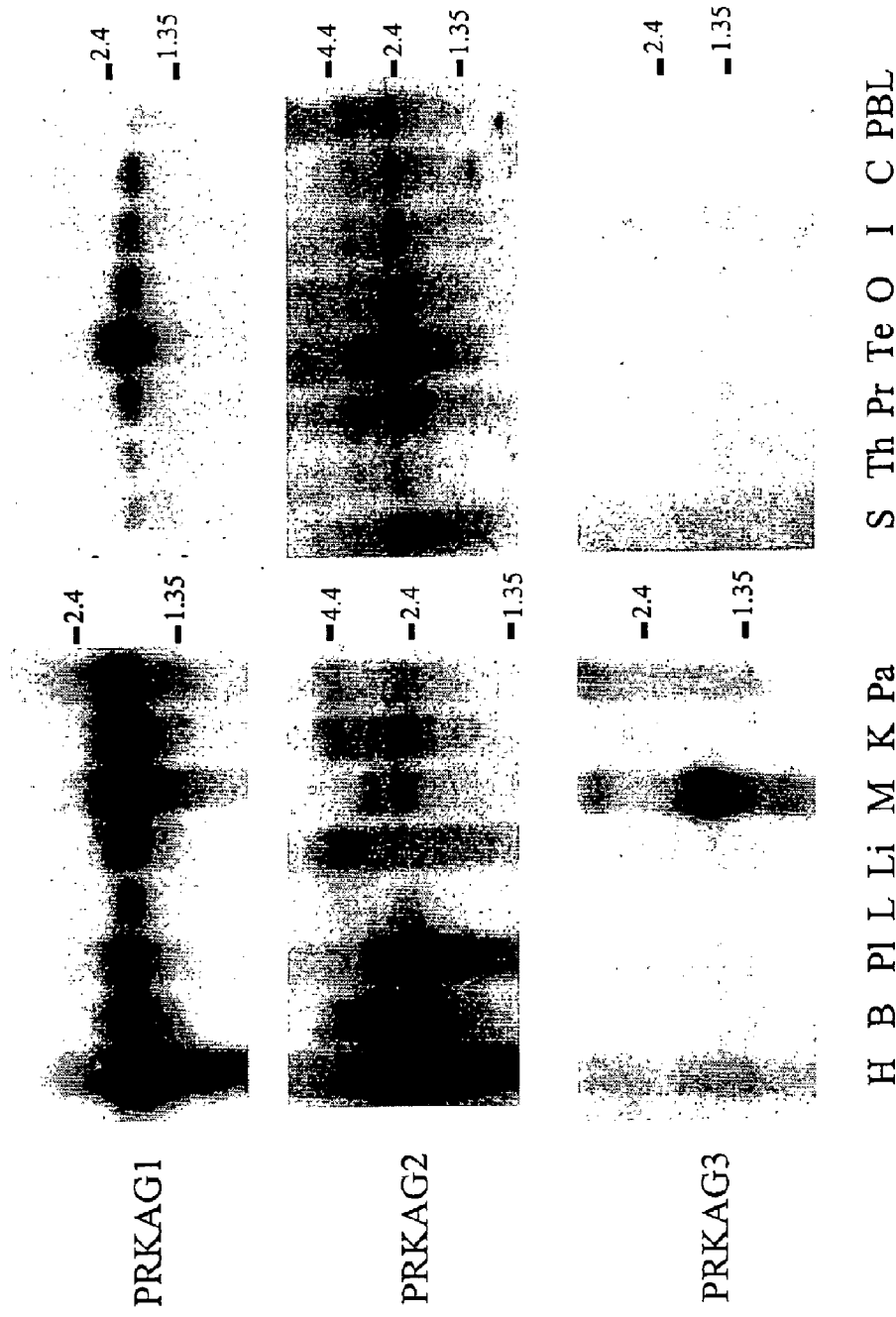
FIG. 5 shows the result of hybridisation analysis of a human multiple tissue northern blot using human PRKAG1, human PRKAG2, and porcine PRKAG3 probes. H: Heart; B: Brain; Pl: Placenta; L: Lung; Li: Liver; M: Skeletal muscle; K: Kidney; Pa: Pancreas; S: Spleen; Th: Thymus; P: Prostate; T: Testis; O: Ovary; I: Small intestine; C: Colon (mucosal lining); PBL: Peripheral Blood Leukocyte. (26:9-25)

Legend of FIG. 5:

H: Heart, B: Brain, Pl: Placenta, L: Lung, Li: Liver, M: Skeletal muscle, K: Kidney, Pa: Pancreas, S: Spleen, Th: Thymus, P: Prostate, T: Testis, O: Ovary, I: Small intestine, C: Colon (mucosal lining), PBL: Peripheral Blood Leukocyte.

While the PRKAG1 and PRKAG2 probes showed a broad tissue distribution of expression, PRKAG3 showed a distinct muscle-specific expression. This result is also supported by the human EST database where multiple ESTs representing PRKAG1 and PRKAG2 have been identified in various cDNA libraries whereas a single EST (GenBank entry AA178898) representing PRKAG3 has been obtained from a muscle cDNA library. The muscle-specific expression of PRKAG3 and the lack of expression in liver are entirely consistent with the phenotypic effect of RN⁻, namely that glycogen content is altered in muscle but normal in liver (ESTRADE et al., Comp Biochem. Physiol. 104B, 321-326, 1993).

PRKAG3 sequences were determined from rn⁺/rn⁺ and RN⁻/RN⁻ homozygotes by RT-PCR analysis. A comparison revealed a total of seven nucleotide differences four of which were nonsynonymous substitutions was found between the sequence from rn⁺ and RN⁻ animals, as shown in Table 3 below. Screening of these seven SNPs with genomic DNA from additional rn⁺ and RN⁻ pigs of different breeds revealed five different PRKAG3 alleles, but only the R41Q missense substitution was exclusively associated with RN⁻. This nonconservative substitution occurs in CBS1 which is the most conserved region among isotypic forms of the AMPK γ chain and arginine at this residue (number 70 in PRKAG1) is conserved among different isoforms of mammalian AMPK γ sequences as well as in the corresponding *Drosophila* sequence (FIG. 3). A simple diagnostic DNA test for the R41Q mutation was designed based on the oligonucleotide ligation assay (OLA; LANDEGREN et al., Science, 241, 1077-1080, 1988). Screening a large number of RN⁻ and rn⁺ animals from the Hampshire breed as well as large number of rn⁺ animals from other breeds showed that the 41Q allele was present in all RN⁻ animals but not found in any rn⁺ animals, as shown in Table 4 below. The absence of the 41Q allele from other breeds is consistent with the assumption that the RN⁻ allele originated in the Hampshire breed; the allele has not yet been found in purebred animals from other breeds. In conclusion, the results provide convincing evidence that PRKAG3 is identical to the RN gene and that the R41Q substitution most likely is the causative mutation.

TABLE 3

Comparison of the PRKAG3 sequences associated with the rn⁺ and RN⁻ alleles in different pig populations[a]

| RN allele | nt83 | nt152 | _____Codon_____ | | | | | Population[b] |
|---|---|---|---|---|---|---|---|---|
| | | | 34 | 35 | 40 | 41 | 213 | |
| RN⁻ | ACC T | CTC L | GCC A | CTG L | GTC V | CAA Q | TCT S | H |
| rn⁺ | --- - | --- - | --- - | --- - | --- - | -G- R | --- - | L, LW, WB |
| rn⁺ | --- - | -C- P | --T - | T-- - | --- - | -G- R | --C - | H, L, LW, M, WB |
| rn⁺ | -A- N | -C- P | --T - | T-- - | --- - | -G- R | --C - | D, H |
| rn⁺ | --- - | -C- P | --T - | T-- - | A-- I | -G- R | --C - | H, LW, WB, D, L |

Nucleotide and codon numbers refer to the numbering of the sequence SEQ ID NO: 1
H = Hampshire, L = Landrace, LW = Large White, M = Meishan, WB = Wild Boar, D = Duroc
ND = not determined, "-" indicates identity to the top sequence.

TABLE 4

| | Genotype at nucleotide 593[d] | | | |
|---|---|---|---|---|
| RN phenotype | A/A | G/A | G/G | Total |
| RN⁻ Hampshire[a] | 40 | 87 | 0 | 127 |
| RN⁻ Hampshire[a,b] | 0 | 13 | 0 | 13 |
| rn⁺ Hampshire[a] | 0 | 0 | 60 | 60 |
| rn⁺, other breeds[c] | 0 | 0 | 488 | 488 |

[a]represent both French and Swedish Hampshire populations
[b]heterozygosity RN⁻/rn⁺ deduced using pedigree information
[c]breeds: Angler Saddleback, n = 31; Blond Mangalitza, n = 2; Bunte Bentheimer, n = 16; Duroc, n = 160; Göttinger Minipig, n = 4; Landrace, n = 83; Large White, n = 72; Meishan, N = 8; Piétrain, n = 75; Red Mangalitza, n = 5; Rotbunte Husumer, n = 15; Schwalbenbauch Mangalitza, n = 7; Schwäbisch Hällische, n = 2; European Wild Boar, N = 5; Japanese Wild Boar, n = 3.
[d]refers to the nucleotide numbers of SEQ ID NO: 1

Without being bound to any particular mechanism, it may be hypothesised that the AMPX heterotrimer including PRKAG3 is involved in the regulation of glucose transport into skeletal muscle.

It has recently been reported that AMPX activation induced by the AMP analogue AICAR or by muscle contraction leads to an increased glucose uptake in skeletal muscle (BERGERON et al., Am. J. Physiol., 276, E938-944, 1999; HAYASHI et al., Diabetes. 47, 1369-1373, 1998). If this is the function of the AMPK heterotrimer including PRKAG3, R41Q may be a gain-of-function mutation causing a constitutively active holoenzyme, for instance due to the loss of an inactivating allosteric site. If so, the reduced AMPK activity in RN⁻ animals is likely to reflect feed-back inhibition due to the high-energy status of the muscle. An increased uptake of glucose to skeletal muscle is expected to lead to an increase in muscle glycogen content as observed in RN⁻ animals. It has been shown that overexpression of glucose transporter 4 (GLUT4) in transgenic mice leads to increased uptake of glucose and increased glycogen storage (TREADWAY et al., J. Biol. Chem., 269, 29956-29961, 1994). This type of gain-of-function model is consistent with the dominance of RN⁻ as the presence of a single unregulated copy would have a large effect on AMPK enzyme activity.

An alternative hypothesis on the functional significance of the R41Q substitution associated with the RN⁻ allele may also be proposed. Based on the established roles of the yeast SNF1 enzyme in utilisation of glycogen and of mammalian AMPK for inhibiting energy-consuming pathways and stimulating energy-producing pathways, activated AMPK is expected to inhibit glycogen synthesis and stimulate glycogen degradation. If this is the functional role of the isoform(s) containing the PRKAG3 product, the R41Q substitution would be a loss-of-function mutation or a dominant-negative mutation locking the AMPK heterotrimer in an inactive state, and thus inhibiting AMP activation and glycogen degradation. In these cases the phenotypic effect should be explained by haplo-insufficiency, since RN⁻ appears fully dominant.

R41 Q may thus be a dominant negative mutation, but only if it interferes with multiple isoforms since the major AMPK activity in muscle appears to be associated with the PRKAG1 and 2 isoforms [CHEUNG, et al. *Biochem. J.* 246, 659 (2000)].

The distinct phenotype of the RN⁻ mutation indicates that PRKAG3 plays a key role in the regulation of energy metabolism in skeletal muscle. For instance, PRKAG3 is likely to be involved in the adaptation to physical exercise, which is associated with increased glycogen storage. It is also conceivable that loss-of-function mutations in PRKAG3 (or other AMPK genes) may predispose individuals to noninsulin-dependent diabetes mellitus, and AMPK isoforms are potential drug targets for treatment of this disorder.

EXAMPLE 2

Detection of the R41Q Substitution in PIG PRKAG3

A part of PRKAG3 including codon 41 was amplified in 10 μl reactions containing 100 ng genomic DNA, 0.2 mM dNTPs, 1.5 mM $MgCl_2$, 4.0 pmol of both forward (AMPKG3F3:5'-GGAGCAAATGTGCAGACAAG-3') (SEQ ID NO:33) and reverse (AMPKG3R2:5'-CCCAC-GAAGCTCTGCTTCTT-3') (SEQ ID NO:34) primer, 10% DMSO, 1 U of Taq DNA polymerase and reaction buffer (ADVANCED BLOTECH, London, UK). The cycling conditions included an initial incubation at 94° for 5 min followed by 3 cycles at 94° C. (1 min), 57° C. (1 min) and 72° C. (1 min), and 35 cycles of 94° C. (20 sec), 55° C. (30 sec) and 72° C. (30 sec). Allele discrimination at nucleotide position 122 was done using the oligonucleotide ligation assay (OLA, LANDEGREN, et at, Science, 241, 1077-1080, 1988). The OLA method was carried out as a gel-based assay. Each 10 μl OLA reaction contained 0.5 pmol of each probe SNPRN-A (5'Hex-TGGCCAACGGCGTCCA-3') (SEQ ID NO:35), SNPRN-G (5'ROX-GGCCAACGGCGTCCG-3') (SEQ ID NO:36) and SNRPN-Common (5' phosphate-AGCGGCAC-CTTTGTGAAAAAAAAAA-3') (SEQ ID NO:37), 1.5 U of thermostable AMPLIGASE and reaction buffer (EPICENTRE TECHNOLOGIES, Madison, Wis.) and 0.5 μl of the AMPKG3F3/AMPKG3R2 PCR product. After an initial incubation at 95° C. for 5 min, the following thermocycling profile was repeated 10 times: denaturation at 95° C. (30 sec), and probe annealing and ligation at 55° C. (90 sec). After OLA cycling, 1 μl of product was heat denatured at 94° C. (3 min), cooled on ice, and loaded onto 6% polyacrylamide denaturing gel for electrophoresis on an ABI377 DNA sequencer (PERKIN ELMER, Foster City, USA). The resulting fragment lengths and peak fluorescence were analyzed using GENESCAN software (PERKIN ELMER, Foster City, USA).

The OLA-based method for the R41Q mutation was used to determine the genotype of DNA samples collected from 68 Swedish Hampshire animals phenotyped as either RN⁻ or rn⁺ based on their glycolytic potential (GP) value. FIG. 6 illustrates typical OLA results from the three possible genotypes. All RN⁻ animals were scored as homozygous A/A (n=28) or heterozygous A/G (n=36) at nucleotide position 122 whereas the rn⁺ animals were homozygous G/G (n=4) at this position.

EXAMPLE 3

Predicting the Presence of the RN⁻ Allele Using a Closely Linked Microsatellite, MS127B1

A microsatellite 127B1 (MS127B1) was cloned from BAC 127G7 containing pig PRKAG3. The BAC clone was digested with Sau3AI and the restriction fragments subcloned into the BamHI site of pUC18. The resulting library was probed with a $(CA)_{15}$ oligonucleotide probe labeled with [γ-32P]-dATP. Strongly hybridizing clones were sequenced and primers for PCR amplification of microsatellite loci were designed. Ten μl PCR reactions were performed containing 100 ng genomie DNA, 0.2 mM dNTPs, 1.5 mM $MgCl_2$, 4.0 pmol of both forward (MS127B1F:5'-Fluorescein-CAAACTCTTCTAGGCGTGT-3') (SEQ ID NO:38) and reverse (MS127B1R:5'-GTTTCTGGAACTTCCATATGC-CATGG-3') (SEQ ID NO:39) primers, and 1 U of Taq DNA polymerase and reaction buffer (ADVANCED BIOTECH, London, UK). The cycling conditions included an initial incubation at 94° C. for 5 min followed by 3 cycles at 94° C. (1 min), 57° C. (1 min) and 72° C. (1 min), and 35 cycles of 94° C. (20 sec), 55° C. (30 sec) and 72° C. (30 sec). The PCR products (0.3 μl) were separated using 4% polyacrylamide denaturing gel eleetrophoresis on an ABI1377 DNA sequencer (PERKIN ELMER, Foster City, USA). The resulting fragment lengths were analyzed using the GENESCAN and GENOTYPER software (PERKIN ELMER, Foster City, USA).

The method was used to determine the genotype of DNA samples collected from 87 Swedish Hampshire animals phenotyped as either RN⁻ or rn⁺ based on their glycolytic potential (GP) value. Allele 108 (bp) showed a complete association to the RN⁻ allele in this material as all RN⁻ (RN⁻/RN⁻ or RN⁻/rn⁺ animals were homozygous or heterozygous for this allele while no rn⁺ (rn⁺/rn⁺) animals carried this allele, as shown in Table 5 below.

TABLE 5

| Animals | N | Genotype | | | | |
|---|---|---|---|---|---|---|
| | | 94/94 | 94/108 | 94/114 | 100/108 | 108/108 |
| RN− | 80 | 0 | 37 | 0 | 2 | 41 |
| rn+ | 7 | 3 | 0 | 4 | 0 | 0 |

EXAMPLE 4

Detecting the Presence of the RN⁻ Allele Using a PCR-RFLP Test

The RN⁻ mutation inactivates a BsrBI site GAG^CGG/CTC^GCC (BsrBI RE site is not palindromic). At that site, the RN⁻ sequence is AAGCGG instead of GAGCGG.

A 134 bp long fragment of the RN gene is amplified from porcine genomic DNA. The rn⁺ allele is identified after BsrBI digestion, by detection of two fragments of 83 and 51 bps.

The test is performed as follows:

1° Primer sequences:

Sequence of primers used to amplify the RN mutation region:

```
RNU: 5' GGGAACGATTCACCCTCAAC 3'    (SEQ ID NO:40)
RNL: 5' AGCCCCTCCTCACCCACGAA 3'    (SEQ ID NO:41)
```

To provide an internal control of digestion, a BsrBI site has been added at the extremity of one of the two primers within a 20 bp long tail. The tail permits both creation of a BsrBI site (a shorter tail might be sufficient), and an easy discrimination of uncut fragment from other fragments. The use of tailed primers does not affect efficiency and specificity of amplification.

The sequence of the RNL modified primer including a control tail with a BsrBI site is: RNLBsrA14: 5' $A_5C_2A_7$CCGCTCAGCCCCTCCTCACCCACGAA 3' (SEQ ID NO:42)

2° PCR reaction mixture used:

50 ng DNA 0.5 Unit Taq polymerase (GIBCO BRL)

1.5 mM $mgCL^2$ 200 mM dNTP 0.2 μM each primer

Total reaction volume: 25 μl

3° PCR conditions used (on OMNIGENE HYBAID thermocycler):

1× (5 min 95° C.)

35×(45 sec 57° C., 45 sec 72° C., 45 sec 95° C.)

1× (45 sec 57° C., 15 min 72° C.)

4° Restriction enzyme digestion performed at 37° C. for 2 hours:

10 μl PCR product

1× BsrBI BIOLABS buffer

5 U BsrBI restriction enzyme (BIOLABS)

Total reaction volume: 15 μl

5° Size of fragments produced after PCR using primers with control tail and digestion with BsrBI:

Uncut fragment from RN⁻ or rn⁺ allele: 154 bp

After digestion of fragment amplified from RN⁻ allele: 137 bp+17 bp

After digestion of fragment amplified from rn⁺ allele: 83 bp+54 bp+17 bp

Size difference can be identified either after polyacrylamide, agarose/NUSIEVE or agarose gel electrophoresis.

EXAMPLE 5

Effect of V40I Polymorphism on Glycolytic Potential

Further, a set of 181 rn+/rn+ homozygous animals (R/R at position 41 of SEQ ID NO:2) were analyzed for the V40I polymorphism (referring to position 40 of SEQ ID NO:2) by PCR-RFLP using FokI restriction enzyme. The glycolytic potential was determined in parallel according to the method disclosed by MONIN et al., (Meat Science, 13, 49-63, 1985).

The results are shown in Table 6 below:

TABLE 6

| Genotype at position 40 | Average glycolytic potential | Standard Deviation | Number of typed animals |
|---|---|---|---|
| I/I | 178.30 | 31.13 | 13 |
| V/I | 204.15 | 37.73 | 164 |
| V/V | 210.83 | 38.21 | 104 |

These results show that the V40I polymorphism has a significant effect on the glycolytic potential in skeletal muscle.

The invention claimed is:

1. An isolated gamma subunit of a vertebrate AMP-activated kinase (AMPK), wherein said gamma subunit is a polypeptide comprising at least a sequence having at least 95% identity with the polypeptide of SEQ ID NO: 2 and wherein said gamma subunit forms a heterotrimer with alpha and beta subunits of said AMPK.

2. An isolated polypeptide of claim 1, wherein said polypeptide comprises the sequence of SEQ ID NO: 2.

3. An isolated potypeptide according to claim 1, which is a functionally altered mutant of a gamma subunit of a vertebrate AMPK, wherein said polypeptide has at least a mutation located within a first CBS domain of said gamma subunit, and wherein the mutation is located within the region of the first CBS domain aligned with the region of a potypeptide of SEQ ID NO: 2 spanning from residue 30 to residue 50 and wherein said polypeptide forms a heterotrimer with alpha and beta subunits of said AMPK.

4. The isolated polypeptide of claim 3, wherein the mutation is a R→Q substitution or a V→I substitution.

5. The isolated polypeptide of claim 4 selected from the group consisting of:
   a polypeptide having a sequence resulting from a R→Q substitution at a position corresponding to position 41 in SEQ ID NO: 2; and
   a polypeptide having a sequence resulting from a V→I substitution at the position corresponding to position 40 of SEQ ID NO: 2.

* * * * *

UNITED STATES PATENT AND TRADEMARK OFFICE
CERTIFICATE OF CORRECTION

PATENT NO. : 7,462,693 B2
APPLICATION NO. : 11/626582
DATED : December 9, 2008
INVENTOR(S) : Leif Andersson It is certified that error appears in the above-identified patent and that said Letters Patent is hereby corrected as shown below:

Title Page, Item [54] Title line 2, please delete "AMPX" and insert --AMPK-- therefor;

Column 57, line 10 (Claim 3), please delete "potypeptide" and insert --polypeptide-- therefor;

Column 57, line 15 (Claim 3), please delete "potypeptide" and insert --polypeptide-- therefor.

Signed and Sealed this

Fourteenth Day of April, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,462,693 B2  
APPLICATION NO. : 11/626582  
DATED                 : December 9, 2008  
INVENTOR(S)        : Leif Andersson Page 1 of 1

It is certified that error appears in the above-identified patent and that said Letters Patent is hereby corrected as shown below:

Title Page, Item [54] Title line 2, and Column 1, line 2, please delete "AMPX" and insert --AMPK-- therefor;

Column 57, line 10 (Claim 3), please delete "potypeptide" and insert --polypeptide-- therefor;

Column 57, line 15 (Claim 3), please delete "potypeptide" and insert --polypeptide-- therefor.

This certificate supersedes the Certificate of Correction issued April 14, 2009.

Signed and Sealed this

Fifth Day of May, 2009

JOHN DOLL  
*Acting Director of the United States Patent and Trademark Office*